US009370494B2

(12) United States Patent
Yeo et al.

(10) Patent No.: US 9,370,494 B2
(45) Date of Patent: Jun. 21, 2016

(54) METHODS FOR TREATING HEPATOCELLULAR CARCINOMA

(75) Inventors: Winnie Yeo, Shatin (CN); Nathalie Wong, Shatin (CN)

(73) Assignee: ABRAXIS BIOSCIENCE, LLC, Los Angeles, CA (US)

(*) Notice: Subject to any disclaimer, the term of this patent is extended or adjusted under 35 U.S.C. 154(b) by 0 days.

(21) Appl. No.: 13/583,603

(22) PCT Filed: Mar. 25, 2011

(86) PCT No.: PCT/US2011/030037
§ 371 (c)(1),
(2), (4) Date: Jan. 22, 2013

(87) PCT Pub. No.: WO2011/119988
PCT Pub. Date: Sep. 29, 2011

(65) Prior Publication Data
US 2013/0115296 A1    May 9, 2013

Related U.S. Application Data

(60) Provisional application No. 61/318,153, filed on Mar. 26, 2010.

(51) Int. Cl.
| A61K 31/713 | (2006.01) |
| A61K 31/337 | (2006.01) |
| A61K 9/51 | (2006.01) |
| A61K 38/38 | (2006.01) |
| A61K 31/352 | (2006.01) |
| A61K 45/06 | (2006.01) |

(52) U.S. Cl.
CPC .............. *A61K 9/5169* (2013.01); *A61K 31/337* (2013.01); *A61K 31/352* (2013.01); *A61K 31/713* (2013.01); *A61K 45/06* (2013.01)

(58) Field of Classification Search
CPC combination set(s) only.
See application file for complete search history.

(56) References Cited

U.S. PATENT DOCUMENTS

| 5,362,478 A | 11/1994 | Desai et al. |
| 5,439,686 A | 8/1995 | Desai et al. |
| 5,498,421 A | 3/1996 | Grinstaff et al. |

(Continued)

FOREIGN PATENT DOCUMENTS

| WO | WO 94/18954 A1 | 9/1994 |
| WO | WO 98/14174 A1 | 4/1998 |

(Continued)

OTHER PUBLICATIONS

Wang et al. "Proteomic identification of molecular targets of gambogic acid: Role of stathmin in hepatocellular carcinoma", Proteomics, vol. 9, pp. 242-253, (2009).*

(Continued)

*Primary Examiner* — Ernst V Arnold
*Assistant Examiner* — Kyung Sook Chang
(74) *Attorney, Agent, or Firm* — Morrison & Foerster LLP

(57) ABSTRACT

The present invention provides methods and compositions for treating hepatocellular carcinoma (HCC) by administering a composition comprising nanoparticles that comprise a taxane and an albumin. The invention also provides combination therapy methods of treating HCC comprising administering to an individual an effective amount of a composition comprising nanoparticles that comprise a taxane and an albumin and another agent, such as an agent that inhibits microtubule disassembly.

14 Claims, 6 Drawing Sheets

(56) References Cited

U.S. PATENT DOCUMENTS

| | | |
|---|---|---|
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,916,596 A | 6/1999 | Desai et al. |
| 5,997,904 A | 12/1999 | Magdassi et al. |
| 6,096,331 A | 8/2000 | Desai et al. |
| 6,506,405 B1 | 1/2003 | Desai et al. |
| 6,528,067 B1 | 3/2003 | Magdassi et al. |
| 6,537,579 B1 | 3/2003 | Desai et al. |
| 6,565,842 B1 | 5/2003 | Desai et al. |
| 6,652,884 B2 | 11/2003 | Falciani |
| 6,749,868 B1 | 6/2004 | Desai et al. |
| 6,753,006 B1 | 6/2004 | Desai et al. |
| 7,758,891 B2 | 7/2010 | Desai et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |
| 8,927,019 B2 | 1/2015 | Desai et al. |
| 8,999,396 B2 | 4/2015 | Desai et al. |
| 9,012,518 B2 | 4/2015 | Desai et al. |
| 9,012,519 B2 | 4/2015 | Desai et al. |
| 9,101,543 B2 | 8/2015 | Desai et al. |
| 9,149,455 B2 | 10/2015 | Desai et al. |
| 2003/0185894 A1 | 10/2003 | Zenoni et al. |
| 2003/0187062 A1 | 10/2003 | Zenoni et al. |
| 2003/0199425 A1 | 10/2003 | Desai et al. |
| 2005/0004002 A1 | 1/2005 | Desai et al. |
| 2006/0263434 A1 | 11/2006 | Desai et al. |
| 2007/0082838 A1 | 4/2007 | De et al. |
| 2007/0093547 A1 | 4/2007 | Desai et al. |
| 2007/0116774 A1* | 5/2007 | Desai ............ A61K 9/0019 424/489 |
| 2007/0117744 A1* | 5/2007 | Desai et al. ............ 514/11 |
| 2008/0045584 A1 | 2/2008 | Chi et al. |
| 2008/0255035 A1 | 10/2008 | Trieu et al. |
| 2008/0280987 A1 | 11/2008 | Desai et al. |
| 2009/0163435 A1* | 6/2009 | Bader et al. ............ 514/44 |
| 2009/0263483 A1 | 10/2009 | Desai et al. |
| 2009/0304805 A1 | 12/2009 | Desai et al. |
| 2010/0048499 A1 | 2/2010 | Desai et al. |
| 2010/0166869 A1 | 7/2010 | Desai et al. |
| 2010/0183728 A1 | 7/2010 | Desai et al. |
| 2010/0215751 A1 | 8/2010 | Desai et al. |
| 2010/0297243 A1 | 11/2010 | Desai et al. |
| 2011/0052708 A1 | 3/2011 | Soon-Shiong et al. |
| 2011/0118342 A1 | 5/2011 | De et al. |
| 2011/0151012 A1 | 6/2011 | Desai et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079177 A1 | 3/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |

FOREIGN PATENT DOCUMENTS

| | | |
|---|---|---|
| WO | WO 98/14175 A1 | 4/1998 |
| WO | WO 99/00113 A1 | 1/1999 |
| WO | WO-00/64437 A1 | 11/2000 |
| WO | WO 00/71079 A2 | 11/2000 |
| WO | WO 00/71079 A3 | 11/2000 |
| WO | WO 01/89522 A1 | 11/2001 |
| WO | WO 02/087545 A1 | 11/2002 |
| WO | WO 03/096944 A1 | 11/2003 |
| WO | WO 2004/052401 A2 | 6/2004 |
| WO | WO 2004/052401 A3 | 6/2004 |
| WO | WO 2006/089290 A1 | 8/2006 |
| WO | WO-2007/027819 A2 | 3/2007 |
| WO | WO-2007/027819 A3 | 3/2007 |
| WO | WO 2007/027941 A2 | 3/2007 |
| WO | WO 2007/027941 A3 | 3/2007 |
| WO | WO 2008/027055 A1 | 3/2008 |
| WO | WO 2008/057562 A1 | 5/2008 |
| WO | WO 2008/076373 A1 | 6/2008 |
| WO | WO 2008/109163 A1 | 9/2008 |
| WO | WO 2008/137148 A2 | 11/2008 |
| WO | WO 2008/137148 A3 | 11/2008 |
| WO | WO 2008/150532 A1 | 12/2008 |
| WO | WO 2009/126175 A1 | 10/2009 |
| WO | WO 2009/126401 A1 | 10/2009 |
| WO | WO 2009/126938 A1 | 10/2009 |
| WO | WO 2010/068925 A1 | 6/2010 |
| WO | WO 2010/105172 A1 | 9/2010 |
| WO | WO 2010/118365 A1 | 10/2010 |
| WO | WO 2010/121000 A1 | 10/2010 |
| WO | WO-2011/025838 A1 | 3/2011 |

OTHER PUBLICATIONS

Altmayer, P. et al. (1995). "Propofol Binding to Human Blood Proteins," *Arzneim.-Forsch/Drug. Res.* 45:1053-1056.

(56) References Cited

OTHER PUBLICATIONS

Carter, D.C. et al. (1994). Structure of Serum Albumin, *Adv. Protein Chem.* 45:153-203.
Chan, K.Y-Y. et al. (2006). "Positional Expression Profiling Indicates Candidate Genes in Deletion Hotspots of Hepatocellular Carcinoma," *Modern Pathology* 19:1546-1554.
Chao, Y. et al. (1998). "Phase II and Pharmacokinetic Study of Paclitaxel Therapy for Unresectable Hepatocellular Carcinoma Patients," *British Journal of Cancer* 78*1):34-39.
Curry, S. et al. (Sep. 1998). Crystal Structure of Human Serum Albumin Complexed With Fatty Acid Reveals an Asymmetric Distribution of Binding Sites, *Nat. Struct. Biol.* 5(9):827-835.
Desai, N. et al. (Feb. 15, 2006). "Increased Antitumor Activity, Intratumor Paclitaxel Concentrations, and endothelial Cell Transport of Cremophor-Free, Albumin-Bound Paclitaxel, ABI-007, Compared With Cremophor-Based Paclitaxel," *Clinical Cancer Research* 12(4):1317-1324.
Endicott, J. et al. (1989). "The Biochemistry of P-Glycoprotein-Mediated Multidrug Resistance," *Annual Review of Biochemistry* 58:137-171.
Fehske, K.J. et al. (1981) "The Location of Drug Binding Sites in Human Serum Albumin," *Biochem. Pharamcol.* 30(7):687-692.
Finlayson, J.S. (1980). Albumin Products, *Seminars in Thrombosis and Hemostatsis* 6(2):85-120.
Garrido, M.J. et al. (Nov.-Dec. 1994). "Binding Characteristics of Propofol to Plasma Proteins and Possible Interactions," *Rev. Esp. Anestesiol. Reanim.* 41(6):308-312. (English Summary).
Gish, R.G. et al. (Jul. 20, 2007). "Phase III Randomized Controlled Trial Comparing the Survial of Patients With Unresectable Hepatocellular Carcinoma Treated With Nolatrexed or Doxorubicin," *J. of Clinical Oncology* 25(21):3069-3075.
Goodman and Gilman. (1996). *The Pharamacological Basis of Therapeutics*, 9$^{th}$ ed, McGraw-Hill, New York, New York, Table of Contents, pp. v-xii.
Hauser, C.J. et al. (Jun. 1980). "Oxygen Transport Responses to Colloids and Crystalloids in Critically III Surgical Patients," Surgery, Gynecology and Obstetrics 150(6):811-816.
He, X. et al. (Jul. 16, 1992). "Atomic Structure and Chemistry of Human Serum Albumin," *Nature* 358:209-215.
Honore, S. et al. (2003). "Suppression of Microtubule Dynamics by Discodermolide by a Novel Mechanism is Associated with Mitotic Arrest and Inhibition of Tumor Cell Proliferation," *Mol. Canc. Therap.* 2:1303-1311.
Kragh-Hansen, U. (Feb. 1990). "Structure and Ligand Binding Properties of Human Serum Albumin," *Danish Medical Bulletin* 37(1):57-84.
Martello, L.A. et al. (May 2000). "Taxol and Discodermolide Represent a Synergistic Drug Combination in Human Carcinoma Cell Lines," *Clin. Canc. Res.* 6:1978-1987.
Ng, I.O.L. et al. (2000). "Expression of P-Glycoprotein in Hepatocellular Carcinoma. A Determinant of Chemotherarpy Response," *American J. of Clinical Pathology* 113:355-363.
O'Dwyer, P.J. et al. (Oct. 1, 2006). "Uridine Diphosphate Glucuronosyltransferase (UGT) 1A1 and Irinotecan: Practical Pharmacogenomics Arrives in Cancer Therapy," *J. Clinical Oncology* 24(28):4534-4538.
Paál, K. et al. (2001). "High Affinity Binding of Paclitaxel to Human Serum Albumin," *Eur. J. Biochem.* 268(7):2187-2191.
Park J-G. et al. (May 4, 1994). MDR1 Gene Expression: Its Effect on Drug Resistance to Doxorubicin in Human Hepatocellular Carcinoma Cell Lines, *J. of the National Cancer Institute* 86(9):700-705.
Parkin, D. M. (Sep. 2001). "Global Cancer Statistics in the Year 2000," *Lancet Oncology* 2:533-543.
Purcell, M. et al. (2000). "Interaction of Taxol with Human Serum Albumin," *Biochim. Biophys. Acat*1478(a):61-68.
Ramanathan, R.K. et al. (Jun. 20, 2006). "Phase II Study of Lapatinib, a Dual Inhibitor of Epidermal Growth Factor Receptor (EGFR) Tyrosine Kinase 1 and 2 (Her2/Neu) in Patients (pts) With Advanced biliary Tree Cancer (BTC) or Hepatocellular Cancer (HCC). A California Consortium (CCC-P) Trial," *J. of Clincial Oncology* 24(18S\S):4010. (Abstact Only.).
Sugio, S. et al. (1999), "Crystal Structure of Human Serum Albumin at 2.5 ç Resolution," *Protein Eng.* 12(6):439-446.
Tullis, J.L. (Jan. 24, 1977). "Albumin. 1. Background and Use," *JAMA* 237(4):355-360.
Tullis, J.L. (Jan. 31, 1977). "Albumin. 2. Guidelines for Clincial use" *JAMA* 237(5):460-463.
Urien, S. et al. (1996). "Docetaxel Serum Protein Binding With High Affinity to Alpha$_1$-Acid Giycoprotein," *Invest New Drugs* 14:147-151.
Vorum, H. (Nov. 1999). "Reversible Ligand Binding to Human Serum Albumin," *Danish Medical Bulletin* 46(5):379-399.
Wong, N. et al. (Feb. 1, 2005). "Transcriptional Profiling Identifies Gene Expression changes Associated with IFN-α Tolerance in Hepatitis C-Related Hepatocellular Carcinoma Cells," *Clinical Cancer Research* 11:1319-1326.
Yeo, W. et al. (Oct. 19, 2005). "A Randomized Phase III Study of Doxorubicin Versus Cisplatin/interferon α-2b/Doxorubicin/Fluorouracil (PIAF) Combination Chemotherapy for Unresectable Hepatocellular Carcinoma," *J. of the National Cancer Institute* 97(20):1532-1538.
Supplementary European Search Report and European Search Opinion mailed on Aug. 2, 2013, for European Patent Application No. 11760333.2, filed on Mar. 25, 2011, five pages.
International Search Report mailed on Jun. 8, 2011, for PCT Patent Application No. PCT/US2011/030037, filed on Mar. 25, 2011, 2 pages.
Written Opinion mailed on Jun. 8, 2011, for PCT Patent Application No. PCT/US2011/030037, filed on Mar. 25, 2011, 6 pages.
U.S. Appl. No. 13/777,980, filed Feb. 26, 2013, for Desai et al.
U.S. Appl. No. 13/777,988, filed Feb. 26, 2013, for Desai et al.
U.S. Appl. No. 13/779,625, filed Feb. 27, 2013, for Desai et al.
U.S. Appl. No. 13/781,479, filed Feb. 28, 2013, for Desai et al.
U.S. Appl. No. 13/781,489, filed Feb. 28, 2013, for Trieu et al.
U.S. Appl. No. 13/781,480, filed Feb. 28, 2013, for Yeo et al.
U.S. Appl. No. 13/782,990, filed Mar. 1, 2013, for Desai et al.
U.S. Appl. No. 13/782,984, filed Mar. 1, 2013, for Desai et al.
U.S. Appl. No. 13/783,122, filed Mar. 1, 2013, for Desai et al.
U.S. Appl. No. 13/701,001, internationally filed May 20, 2011, for Desai et al.
U.S. Appl. No. 13/782,992, filed Mar. 1, 2013, for Desai et al.
U.S. Appl. No. 13/794,705, filed Mar. 12, 2013, for Desai et al.
U.S. Appl. No. 13/791,841, filed Mar. 12, 2013, for Desai et al.
U.S. Appl. No. 13/794,480, filed Mar. 12, 2013, for Desai et al.
U.S. Appl. No. 13/794,486, filed Mar. 12, 2013, for Heise et al.
U.S. Appl. No. 13/794,712, filed Mar. 11, 2013, for Pierce et al.
U.S. Pat. No. 8,968,752, Mar. 2015, Desai et al. (Withdrawn).
Botos, E, et al, (2008). "Caveolin-1 is transported to multi-vesicular bodies after albumin-induced endocytosis of caveolae in HepG2 cells", *J. Cell. Mol. Med.*, vol. 12(5A):1632-1639.
Iancu, C. et al. (2000). "Taxol and Anti-Stathmin Therapy: A Synergistic Combination that Targets the Mitotic Spindle", *Cancer Res.*, 60:3537-3541.
Miele, E. et al. (2009). "Albumin-bound formulation of paclitaxel (Abraxan® ABI-007) in the treatment of breast cancer", *International Journal of Nanomedicine*, 4:99-105.
Singer, S. et al. (Sep. 2007). "Protumorigenic Overexpression of Stathmin/Op18 by Gain-of Function Mutation in p53 in Human Hepatocarcinogenesis," *Hepatology* 46(3):759-768.
U.S. Appl. No. 14/273,319, filed May 8, 2014, for Desai et al.
U.S. Appl. No. 14/362,382, filed Jun. 2, 2014, for Foss et al.
U.S. Appl. No. 14/468,127, filed Aug. 25, 2014, for Desai et al.
U.S. Appl. No. 14/505,452, filed Oct. 2, 2014, for Desai et al.
U.S. Appl. No. 14/526,358, filed Oct. 28, 2014, for Desai et al.
U.S. Appl. No. 14/550,509, filed Nov. 21, 2014, for Desai et al.
U.S. Appl. No. 14/626,678, filed Feb. 19, 2015, by Desai et al.
U.S. Appl. No. 14/631,671, filed Feb. 25, 2015, by Desai et al.
U.S. Appl. No. 14/660,872, filed Mar. 17, 2015, by Desai et al.
U.S. Appl. No. 14/714,131, filed May 15, 2015, by Seward et al.
U.S. Appl. No. 14/834,331, filed Aug. 24, 2015, by Desai et al.

(56) References Cited

OTHER PUBLICATIONS

U.S. Appl. No. 14/835,485, filed Aug. 25, 2015, by Desai et al.
U.S. Appl. No. 14/771,783, internationally filed Mar. 10, 2014, by Benettaib et al.
U.S. Appl. No. 14/772,335, internationally filed Mar. 10, 2014, by Desai et al.
U.S. Appl. No. 14/772,725, internationally filed Mar. 13, 2014, for Desai et al.

* cited by examiner

Fig 3.
Hep3B
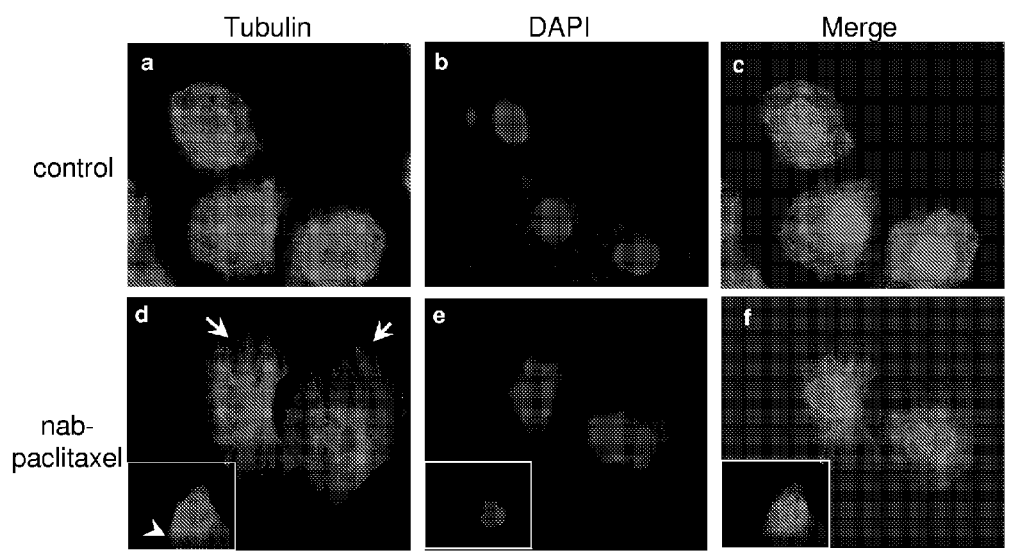
SK-Hep1
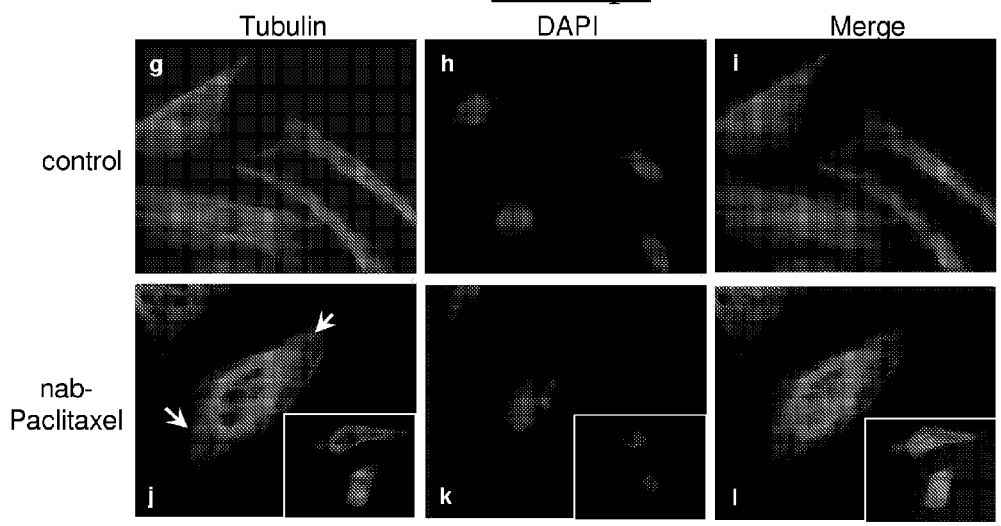

METHODS FOR TREATING HEPATOCELLULAR CARCINOMA

CROSS REFERENCE TO RELATED APPLICATIONS

The patent application is a National Phase filing under 35 U.S.C. §371 of International Application No. PCT/US2011/030037 having an international filing date of Mar. 25, 2011, which claims the benefit of priority under 35 U.S.C. §119(e) of U.S. Provisional Application No. 61/318,153, filed Mar. 26, 2010, the entire content of each of which is incorporated herein by reference in their entirety.

TECHNICAL FIELD

The present invention relates to methods and compositions for the treatment of hepatocellular carcinoma (HCC) by administering compositions comprising nanoparticles that comprise a taxane and an albumin.

BACKGROUND

Hepatocellular carcinoma (HCC) is the fifth most common cancer worldwide and the third most common cause of cancer-related deaths. See Parkin D. M., *Lancet Oncology* 2:533-43 (2001). The disease is often diagnosed late in the course of clinical manifestation. As a result, only 10-15% of patients are candidates for curative surgery. For the majority of HCC patients, systemic chemotherapies or supportive therapies are the mainstay treatment options. Nevertheless, most chemotherapeutic agents show limited effectiveness and have not been able to improve patient survival. See e.g., Yeo W. et al., *J. of the National Cancer Institute* 97:1532-8 (2005), Gish R. G. et al., *J. of Clinical Oncology* 25:3069-75 (2007), Ramanathan R. K. et al., *J. of Clinical Oncology* 24:4010 (2006), and O'Dwyer P. J. et al., *J. of Clinical Oncology* 24:4143 (2006). Recent Phase III randomized trial of Sorafenib, an oral multi-kinase inhibitor of the VEGF receptor, PDGF receptor, and Raf, on hepatitis B-related HCC patients showed for the first time to prolong survival of advanced stage patients. See Cheng A. L. et al., Lancet Oncology 10:25-34 (2009). However, the median overall survival only increased from 4.2 months in the placebo group to 6.5 months in the treatment group. Moreover, HCC is frequently chemotherapy-resistant and known to over-express multi-drug resistance genes, such as MDR1 (P-gp) and the multi-drug resistance proteins (MRPs). See e.g., Ng I. et al., American J. of Clinical Pathology 113:355-63 (2000), Endicott J. A. et al., *Annual Review of Biochemistry* 58:137-71 (1989), and Park J. G. et al., *J. of the National Cancer Institute* 86:700-5 (1994). The adverse clinical course of most HCC patients underscores much need for more efficacious chemotherapies and development of targeting strategies.

Taxanes (such as paclitaxel and docetaxel) are a class of diterpenoid drugs that have anti-tumor activity against a wide range of human cancers. Paclitaxel was originally isolated from the bark of the Yew tree, and was known to act by interfering with the normal function of microtubule breakdown. Paclitaxel binds to the β subunit of tubulin, the building blocks of microtubules, causing hyper-stabilization of the microtubule structures. The resulting paclitaxel/microtubule structure is unable to disassemble, thereby arresting mitosis and inhibiting angiogenesis. Although paclitaxel has been shown to be effective against various malignant tumor cells such as breast cancer, melanoma, and ovarian cancer, its effectiveness against HCC has been questioned. A phase II clinical trial of paclitaxel for HCC patients was reported in British Journal of Cancer, 78(1), 24-39, 1998, which concluded that paclitaxel had no significant anti-cancer effect in HCC patients. Docetaxel, on the other hand, was reported to be more active against HCC cells than paclitaxel. US Patent App. No. 2008/0045584.

Albumin-based nanoparticle compositions have been developed as a drug delivery system for delivering substantially water insoluble drugs such as taxanes. See, for example, U.S. Pat. Nos. 5,916,596; 6,506,405; 6,749,868, and 6,537,579, 7,820,788 and also in U.S. Pat. Pub. No. 2007/0082838. The albumin-based nanoparticle technology utilizes the natural properties of the protein albumin to transport and deliver substantially water insoluble drugs to the site of disease. These nanoparticles are readily incorporated into the body's own transport processes and are able to exploit the tumors' attraction to albumin, enabling the delivery of higher concentrations of the active drug in the nanoparticles to the target site. In addition, the albumin-based nanoparticle technology offers the ability to improve a drug's solubility by avoiding the need for toxic chemicals, such as solvents, in the administration process, thus potentially improving safety through the elimination of solvent-related side effects.

The disclosures of all publications, patents, patent applications and published patent applications referred to herein are hereby incorporated herein by reference in their entirety.

BRIEF SUMMARY OF THE INVENTION

The present invention in some embodiments provides a method of treating hepatocellular carcinoma (HCC) in an individual in need thereof, comprising administering to the individual an effective amount of a composition comprising nanoparticles comprising a taxane and an albumin (hereinafter also referred to as "the nanoparticle composition" or "taxane nanoparticle composition"). In some embodiments, the taxane is paclitaxel. In some embodiments, the taxane is docetaxel. In some embodiments, the albumin is human serum albumin. In some embodiments, the nanoparticles comprise paclitaxel (or docetaxel) coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (Abraxane®)). In some embodiments, the composition is Nab-paclitaxel (Abraxane®).

Thus, for example, in some embodiments, there is provided a method of treating hepatocellular carcinoma (HCC) in an individual in need thereof, comprising administering to the individual an effective amount of a composition comprising nanoparticles comprising a taxane and an albumin, wherein the taxane in the nanoparticles is coated with the albumin. In some embodiments, there is provided a method of treating hepatocellular carcinoma (HCC) in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm). In some embodiments, there is provided a method of treating hepatocellular carcinoma (HCC) in an individual in need thereof, comprising administering to the individual an effective amount of a composition comprising nanoparticles comprising a taxane and an albumin, wherein the taxane in the nanoparticles is coated with the albumin, and wherein the average particle size of the nanoparticles in the nanoparticle composition is no greater than about 200 nm (such as less than about 200 nm). In some embodiments, there is provided a method of treating hepatocellular carcinoma (HCC) in an individual in need thereof, comprising administering to the individual an effective amount of a composition comprising Nab-paclitaxel. In some embodiments, there is provided a method of treating hepatocellular carcinoma (HCC) in an individual in need thereof, comprising administering to the individual an effective amount of Nab-paclitaxel.

In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion.

Also provided are combination therapy methods for treating HCC. Thus, for example, in some embodiments, there is provided a method of treating HCC in an individual in need thereof, comprising administering to the individual (a) an effective amount of a composition comprising nanoparticles comprising taxane and albumin; and (b) an effective amount of at least one other agent, wherein said other agent inhibits microtubule disassembly. The nanoparticle composition and the other agent can be administered simultaneously or sequentially. In some embodiments, the nanoparticle composition and the other agent are administered concurrently. In some embodiments, the taxane is paclitaxel. In some embodiments, the taxane is docetaxel. In some embodiments, the albumin is human serum albumin. In some embodiments, the nanoparticles comprise paclitaxel (or docetaxel) coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (Abraxane®)). In some embodiments, the composition is Nab-paclitaxel (Abraxane®).

In some embodiments, the other agent inhibits a molecule that promotes microtubule disassembly either directly or indirectly. In some embodiments, the other agent inhibits the activity of the molecule that promotes microtubule disassembly. In some embodiments, the agent inhibits the expression of the molecule that promotes microtubule assembly. In some embodiments, the other agent inhibits a molecule selected from the group consisting of ABP1, ARHGAP4, HSPA8, LCP1, PACSIN2, RUNX1T1, STMN1, Tubulin, and TUBB4.

In some embodiments, the other agent activates a molecule that promotes microtubule assembly either directly or indirectly. In some embodiments, the other agent enhances the activity of the molecule that promotes microtubule assembly. In some embodiments, the agent increases the expression of the molecule that promotes microtubule assembly. In some embodiments, the other agent activates a molecule selected from the group consisting of ABI1, BCL2L11, CDC42, CHRM3, CNN3, CSMD1, DDOST, DOCK7, EHMT2, ENAH, ERMAP, ERLF1, HDAC5, LDLRAP1, MCF2, OLA1, RASA1, SHC2, STMN2, and TRIP10.

In some embodiments, there is provided a method of treating HCC in an individual in need thereof, comprising administering to the individual (a) an effective amount of a composition comprising nanoparticles comprising taxane and albumin; and (b) an effective amount of an agent that inhibits STMN1 (Stathmin 1). In some embodiments, the nanoparticle composition and the agent that inhibits STMN1 have synergistic effect on treating HCC. In some embodiments, the agent that inhibits STMN1 sensitizes the HCC cells to the treatment with the nanoparticle composition.

In some embodiments, the agent inhibits the activity of STMN1. In some embodiments, the agent inhibits the binding of STMN1 to tubulin. In some embodiments, the agent increases phosphorylation of STMN1. In some embodiments, the agent is a molecule of the Xanthone family. In some embodiments, the agent is a gamboge or a derivative thereof. Gamboge and derivatives include, for example, gambogic acid (GA) and gembogenic acid (GEA).

In some embodiments, the agent inhibits the expression of STMN1. In some embodiments, the agent is an anti-STMN1 ribozyme (such as Rz184 and Rz305). In some embodiments, the agent is an antisense oligonucleotide against STMN1. In some embodiments, the agent is a small interference RNA (siRNA) against STMN1. Thus, for example, in some embodiments, there is provided a method of treating HCC in an individual in need thereof, comprising administering to the individual (a) an effective amount of a composition comprising nanoparticles comprising taxane and albumin; and (b) an effective amount of a composition that inhibits STMN1, wherein the composition comprises an siRNA against STMN1. In some embodiments, the composition comprises more than one siRNA against STMN1.

Thus, for example, in some embodiments, there is provided a method of treating hepatocellular carcinoma (HCC) in an individual in need thereof, comprising administering to the individual: (a) an effective amount of a composition comprising nanoparticles comprising a taxane and an albumin, wherein the taxane in the nanoparticles is coated with the albumin, and (b) an effective amount of a composition that inhibits STMN1 (such as a composition comprising an siRNA against STMN1). In some embodiments, there is provided a method of treating hepatocellular carcinoma (HCC) in an individual in need thereof, comprising administering to the individual (a) an effective amount of a composition comprising nanoparticles comprising a taxane and an albumin, wherein the average particle size of the nanoparticles in the nanoparticle composition is no greater than about 200 nm (such as less than about 200 nm), and (b) an effective amount of a composition that inhibits STMN1 (such as a composition comprising an siRNA against STMN1).

In some embodiments, there is provided a method of treating hepatocellular carcinoma (HCC) in an individual in need thereof, comprising administering to the individual (a) an effective amount of a composition comprising nanoparticles comprising a taxane and an albumin, wherein the taxane in the nanoparticles is coated with the albumin, and wherein the average particle size of the nanoparticles in the nanoparticle composition is no greater than about 200 nm (such as less than about 200 nm), and (b) an effective amount of a composition that inhibits STMN1 (such as a composition comprising an siRNA against STMN1). In some embodiments, there is provided a method of treating hepatocellular carcinoma (HCC) in an individual in need thereof, comprising administering to the individual (a) an effective amount of a composition comprising Nab-paclitaxel, and (b) an effective amount of a composition that inhibits STMN1 (such as a composition comprising an siRNA against STMN1). In some embodiments, there is provided a method of treating hepatocellular carcinoma (HCC) in an individual in need thereof, comprising administering to the individual (a) an effective amount of Nab-paclitaxel, and (b) an effective amount of a composition that inhibits STMN1 (such as a composition comprising an siRNA against STMN1).

HCC that can be treated with methods described herein include, but are not limited to, liver cell carcinomas, fibrolamellar variants of HCC, and mixed hepatocellular cholangiocarcinomas. In some embodiments, the HCC is any of early stage HCC, non-metastatic HCC, primary HCC, advanced HCC, locally advanced HCC, metastatic HCC, HCC in remission, recurrent HCC, HCC in an adjuvant setting, or HCC in a neoadjuvant setting. In some embodiments, the HCC is resistant to the treatment with a non-nanoparticle formulation of a chemotherapeutic agent (such as non-nanoparticle formulation of paclitaxel).

The methods described herein can be used for any one or more of the following purposes: alleviating one or more symptoms of HCC, delaying progressing of HCC, shrinking tumor size in HCC patient, inhibiting HCC tumor growth, prolonging overall survival, prolonging disease-free survival, prolonging time to HCC disease progression, preventing or delaying HCC tumor metastasis, reducing (such as eradiating) preexisting HCC tumor metastasis, reducing incidence or burden of preexisting HCC tumor metastasis, preventing recurrence of HCC.

Also provided are compositions (such as pharmaceutical compositions), medicine, kits, and unit dosages useful for methods described herein.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIG. 3 shows the microtubule morphology in Hep3B and SK-HEP1 cells treated with Nab-Paclitaxel. Cells treated with 5 ng/ml Nab-Paclitaxel for 24 hour were fixed in 4% paraformaldehyde, and stained for β-tubulin (a, d, g, j). Nuclei were counterstained with DAPI (b, e, h, k). (a to c): Hep3B control; (d to f): Nab-Paclitaxel treated Hep3B; (g to i): SK-HEP1 control; (j to l): Nab-Paclitaxel treated SK-HEP1. Inserts in figures (d to f) and (j to l) are captures from a different field from the same slide. Nab-Paclitaxel treated cells showed a higher degree of microtubule polymerization (arrows). Representative images from two independent experiments are shown.

FIG. 6A shows the level of STMN1 at day 1 and day 3 after siRNA knockdown. STMN1 expression was determined by Western blot (FIG. 6A). Images are representative of three independent experiments. FIG. 6B shows that silencing of STMN1 inhibits Hep3B cell viability by ~40% on day 3. Data are expressed as means±SD of three independent experiments ($P<0.01$, *$P<0.001$ compared to siMock group). FIG. 6C shows that silencing of STMN1 expression sensitized STMN1-overexpressing cells to anti-microtubule drugs. Hep3B cells transfected with siSTMN1 were treated with Doxorubicin, Paclitaxel and Nab-Paclitaxel for 48 h. Distinct synergistic effect was suggested with Nab-Paclitaxel. Results shown represent mean±SD from 2 or more independent experiments (*$P<0.05$, **$P<0.01$ compared to siMock group).

DETAILED DESCRIPTION OF THE INVENTION

Figure 1:
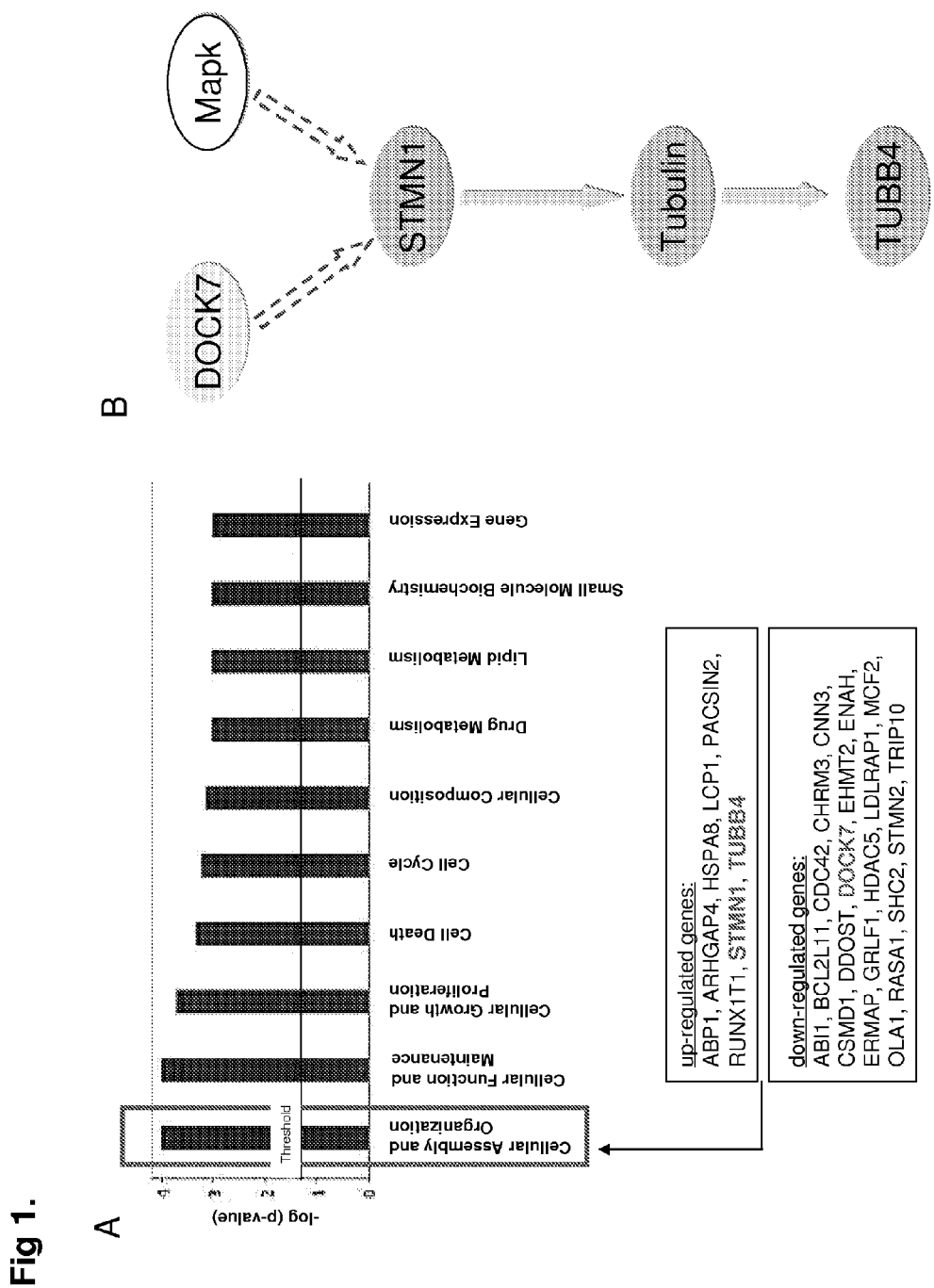
FIG. 1A shows an Ingenuity Pathway Analysis which reveals 10 top ranked functional ontologies in HCC. The up-regulated and down-regulated genes involved in cellular assembly and organization are shown.
FIG. 1B illustrates the STMN1-Tubulin axis path.

The present invention provides methods and compositions for treating HCC by administering a composition comprising nanoparticles comprising a taxane and an albumin. Also provided are methods of combination therapy for treating HCC by administering a composition comprising nanoparticles comprising a taxane and an albumin, along with at least one other agent that inhibits microtubule disassembly (such as an inhibitor of STMN1).

Using in vitro cell viability assays and mouse xenograft studies, we have found that an albumin stabilized nanoparticle formulation of paclitaxel, namely, Nab-paclitaxel, showed an effective IC50 dose that is 15-fold lower than that of the non-nanoparticle formulations of paclitaxel (Paclitaxel or Taxol® and docetaxel (Docetaxel or Taxotere®, and about 450 fold less than Doxorubicin. In vivo animal studies also showed that Nab-paclitaxel readily inhibited Xenograft tumor growth with less toxicity to host cells compared to Paclitaxel, Docetaxel, and Doxorubicin. We have further found that gene silencing of a major microtubule regulatory gene STMN1 in combination with Nab-paclitaxel showed distinct synergistic effect in killing HCC cells. The present invention thus provides methods and compositions for treating HCC by administering a nanoparticle composition of albumin and a taxane, alone or in combination with another agent, such as an agent that inhibits microtubule disassembly (such as an inhibitor of STMN1).

In one aspect, there is provided a method of treating HCC in an individual in need thereof, comprising administering to the individual an effective amount of a composition comprising nanoparticles comprising a taxane and an albumin.

In another aspect, there is provided a method of treating HCC in an individual in need thereof, comprising administering to the individual (a) an effective amount of a composition comprising nanoparticles comprising a taxane and albumin; and (b) an effective amount of at least one other agent, wherein said other agent inhibits microtubule disassembly.

Also provided are compositions (such as pharmaceutical compositions), medicine, kits, and unit dosages useful for the methods described herein.

DEFINITIONS

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of HCC. The methods of the invention contemplate any one or more of these aspects of treatment.

The term "individual" refers to a mammal and includes, but is not limited to, human, bovine, horse, feline, canine, rodent, or primate.

As used herein, an "at risk" individual is an individual who is at risk of developing HCC. An individual "at risk" may or may not have detectable disease, and may or may not have displayed detectable disease prior to the treatment methods described herein. "At risk" denotes that an individual has one or more so-called risk factors, which are measurable parameters that correlate with development of HCC, which are described herein. An individual having one or more of these risk factors has a higher probability of developing cancer than an individual without these risk factor(s).

"Adjuvant setting" refers to a clinical setting in which an individual has had a history of HCC, and generally (but not necessarily) been responsive to therapy, which includes, but is not limited to, surgery (e.g., surgery resection), radiotherapy, and chemotherapy. However, because of their history of HCC, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of HCC means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease.

A method that "delays" development of HCC is a method that reduces probability of disease development in a given time frame and/or reduces the extent of the disease in a given time frame, when compared to not using the method. Such comparisons are typically based on clinical studies, using a statistically significant number of subjects. HCC development can be detectable using standard methods, including, but not limited to, computerized axial tomography (CAT Scan), Magentic Resonance Imaging (MRI), abdominal ultrasound, clotting tests, arteriography, or biopsy. Development may also refer to HCC progression that may be initially undetectable and includes occurrence, recurrence, and onset.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual.

The term "effective amount" used herein refers to an amount of a compound or composition sufficient to treat a specified disorder, condition or disease such as ameliorate, palliate, lessen, and/or delay one or more of its symptoms. In reference to HCC, an effective amount comprises an amount sufficient to cause a tumor to shrink and/or to decrease the growth rate of the tumor (such as to suppress tumor growth) or to prevent or delay other unwanted cell proliferation in HCC. In some embodiments, an effective amount is an amount sufficient to delay development of HCC. In some embodiments, an effective amount is an amount sufficient to prevent or delay recurrence. An effective amount can be administered in one or more administrations. In the case of HCC, the effective amount of the drug or composition may: (i) reduce the number of HCC cells; (ii) reduce tumor size; (iii) inhibit, retard, slow to some extent and preferably stop HCC cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with HCC.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

Methods of Treating HCC

The invention provides methods of treating HCC in an individual (e.g., human) comprising administering to the individual an effective amount of a composition comprising nanoparticles comprising a taxane and an albumin. The present invention also provides methods of treating HCC in an individual (e.g., human) comprising administering to the individual a) an effective amount of a composition comprising nanoparticles comprising a taxane and an albumin; and b) an effective amount of at least one other agent, wherein said other agent inhibits microtubule disassembly. It is understood that reference to and description of methods of treating HCC below is exemplary and that this description applies equally to and includes methods of treating HCC using combination therapy.

In some embodiments, there is provided a method of treating HCC in an individual (e.g., human), comprising administering to the individual an effective amount of a composition comprising nanoparticles comprising a taxane and an albumin (such as human serum albumin). In some embodiments, there is provided a method of treating HCC in an individual (e.g., human), comprising administering to the individual an effective amount of a composition comprising nanoparticles comprising a taxane and an albumin (such as human serum albumin), wherein the taxane in the nanoparticles is coated with the albumin. In some embodiments, there is provided a method of treating HCC in an individual (e.g., human), comprising administering to the individual an effective amount of a composition comprising nanoparticles comprising paclitaxel and an albumin (such as human serum albumin). In some embodiments, there is provided a method of treating HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin.

In some embodiments, there is provided a method of treating HCC in an individual (e.g., human), comprising administering to the individual an effective amount of a composition comprising nanoparticles comprising a taxane and an albumin (such as human serum albumin), wherein the average particle size of the nanoparticles in the composition is no greater than about 200 nm (such as less than about 200 nm). In some embodiments, there is provided a method of treating HCC in an individual (e.g., human), comprising administering to the individual an effective amount of a composition comprising nanoparticles comprising paclitaxel and an albumin (such as human serum albumin), wherein the average particle size of the nanoparticles in the composition is no greater than about 200 nm (such as less than about 200 nm).

In some embodiments, there is provided a method of treating HCC in an individual (e.g., human), comprising administering to the individual an effective amount of a composition comprising nanoparticles comprising a taxane and an albumin (such as human serum albumin), wherein the taxane in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human), comprising administering to the individual an effective amount of a composition comprising Nab-paclitaxel. In some embodiments, there is provided a method of treating HCC in an individual (e.g., human), comprising administering to the individual an effective amount of Nab-paclitaxel.

In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellular cholangiocarcinomas.

Thus, for example, in some embodiments, there is provided a method of treating localized resectable HCC in an individual (e.g., human), comprising administering to the individual an effective amount of a composition comprising nanoparticles comprising a taxane and an albumin (such as human serum albumin). In some embodiments, there is provided a method of treating localized resectable HCC in an individual (e.g., human), comprising administering to the individual an effective amount of a composition comprising nanoparticles comprising a taxane and an albumin (such as human serum albumin), wherein the taxane in the nanoparticles is coated with the albumin. In some embodiments, there is provided a method of treating localized resectable HCC in an individual (e.g., human), comprising administering to the individual an effective amount of a composition comprising nanoparticles comprising paclitaxel and an albumin (such as human serum albumin). In some embodiments, there is provided a method of treating localized resectable HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin.

In some embodiments, there is provided a method of treating localized resectable HCC in an individual (e.g., human), comprising administering to the individual an effective amount of a composition comprising nanoparticles comprising a taxane and an albumin (such as human serum albumin), wherein the average particle size of the nanoparticles in the composition is no greater than about 200 nm (such as less than about 200 nm). In some embodiments, there is provided a method of treating localized resectable HCC in an individual (e.g., human), comprising administering to the individual an effective amount of a composition comprising nanoparticles comprising paclitaxel and an albumin (such as human serum albumin), wherein the average particle size of the nanoparticles in the composition is no greater than about 200 nm (such as less than about 200 nm).

In some embodiments, there is provided a method of treating localized resectable HCC in an individual (e.g., human), comprising administering to the individual an effective amount of a composition comprising nanoparticles comprising a taxane and an albumin (such as human serum albumin), wherein the taxane in the nanoparticles is coated with the albumin, and wherein the average particle size of the nanoparticles in the composition is no greater than about 200 nm (such as less than about 200 nm). In some embodiments, there is provided a method of treating localized resectable HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin, and wherein the average particle size of the nanoparticles in the composition is no greater than about 200 nm (such as less than about 200 nm). In some embodiments, there is provided a method of treating localized resectable HCC in an individual (e.g., human), comprising administering to the individual an effective amount of a composition comprising Nab-paclitaxel. In some embodiments, there is provided a method of treating localized resectable HCC in an individual (e.g., human), comprising administering to the individual an effective amount of Nab-paclitaxel.

In some embodiments, there is provided a method of treating localized unresectable HCC in an individual (e.g., human), comprising administering to the individual an effective amount of a composition comprising nanoparticles comprising a taxane and an albumin (such as human serum albumin). In some embodiments, there is provided a method of treating localized unresectable HCC in an individual (e.g., human), comprising administering to the individual an effective amount of a composition comprising nanoparticles comprising a taxane and an albumin (such as human serum albumin), wherein the taxane in the nanoparticles is coated with the albumin. In some embodiments, there is provided a method of treating localized unresectable HCC in an individual (e.g., human), comprising administering to the individual an effective amount of a composition comprising nanoparticles comprising paclitaxel and an albumin (such as human serum albumin). In some embodiments, there is provided a method of treating localized unresectable HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin.

In some embodiments, there is provided a method of treating localized unresectable HCC in an individual (e.g., human), comprising administering to the individual an effective amount of a composition comprising nanoparticles comprising a taxane and an albumin (such as human serum albumin), wherein the average particle size of the nanoparticles in the composition is no greater than about 200 nm (such as less than about 200 nm). In some embodiments, there is provided a method of treating localized unresectable HCC in an individual (e.g., human), comprising administering to the individual an effective amount of a composition comprising nanoparticles comprising paclitaxel and an albumin (such as human serum albumin), wherein the average particle size of the nanoparticles in the composition is no greater than about 200 nm (such as less than about 200 nm).

In some embodiments, there is provided a method of treating localized unresectable HCC in an individual (e.g., human), comprising administering to the individual an effective amount of a composition comprising nanoparticles comprising a taxane and an albumin (such as human serum albumin), wherein the taxane in the nanoparticles is coated with the albumin, and wherein the average particle size of the nanoparticles in the composition is no greater than about 200 nm (such as less than about 200 nm). In some embodiments, there is provided a method of treating localized unresectable HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin, and wherein the average particle size of the nanoparticles in the composition is no greater than about 200 nm (such as less than about 200 nm). In some embodiments, there is provided a method of treating localized unresectable HCC in an individual (e.g., human), comprising administering to the individual an effective amount of a composition comprising Nab-paclitaxel. In some embodiments, there is provided a method of treating localized unresectable HCC in an individual (e.g., human), comprising administering to the individual an effective amount of Nab-paclitaxel.

In some embodiments, there is provided a method of treating unresectable HCC in an individual (e.g., human), comprising administering to the individual an effective amount of a composition comprising nanoparticles comprising a taxane and an albumin (such as human serum albumin). In some embodiments, there is provided a method of treating unresectable HCC in an individual (e.g., human), comprising administering to the individual an effective amount of a composition comprising nanoparticles comprising a taxane and an albumin (such as human serum albumin), wherein the taxane in the nanoparticles is coated with the albumin. In some embodiments, there is provided a method of treating unresectable HCC in an individual (e.g., human), comprising administering to the individual an effective amount of a composition comprising nanoparticles comprising paclitaxel and an albumin (such as human serum albumin). In some embodiments, there is provided a method of treating unresectable HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin.

In some embodiments, there is provided a method of treating unresectable HCC in an individual (e.g., human), comprising administering to the individual an effective amount of a composition comprising nanoparticles comprising a taxane and an albumin (such as human serum albumin), wherein the average particle size of the nanoparticles in the composition is no greater than about 200 nm (such as less than about 200 nm). In some embodiments, there is provided a method of treating unresectable HCC in an individual (e.g., human), comprising administering to the individual an effective amount of a composition comprising nanoparticles comprising paclitaxel and an albumin (such as human serum albumin), wherein the average particle size of the nanoparticles in the composition is no greater than about 200 nm (such as less than about 200 nm).

In some embodiments, there is provided a method of treating unresectable HCC in an individual (e.g., human), comprising administering to the individual an effective amount of a composition comprising nanoparticles comprising a taxane and an albumin (such as human serum albumin), wherein the taxane in the nanoparticles is coated with the albumin, and wherein the average particle size of the nanoparticles in the composition is no greater than about 200 nm (such as less than about 200 nm). In some embodiments, there is provided a method of treating unresectable HCC in an individual (e.g., human), comprising administering to the individual an effective amount of a composition comprising nanoparticles comprising paclitaxel and an albumin (such as human serum albumin), wherein the paclitaxel in the nanoparticles is coated with the albumin, and wherein the average particle size of the nanoparticles in the composition is no greater than about 200 nm (such as less than about 200 nm). In some embodiments, there is provided a method of treating unresectable HCC in an individual (e.g., human), comprising administering to the individual an effective amount of a composition comprising Nab-paclitaxel. In some embodiments, there is provided a method of treating unresectable HCC in an individual (e.g., human), comprising administering to the individual an effective amount of Nab-paclitaxel.

The methods provided herein can be used to treat an individual (e.g., human) who has been diagnosed with or is suspected of having HCC. In some embodiments, the individual is human. In some embodiments, the individual is at least about any of 35, 40, 45, 50, 55, 60, 65, 70, 75, 80, or 85 years old. In some embodiments, the individual is of Asian ancestry. In some embodiments, the individual is male. In some embodiments, the individual is a female. In some embodiments, the individual has early stage of HCC, non-metastatic HCC, primary HCC, advanced HCC, locally advanced HCC, metastatic HCC, HCC in remission, or recurrent HCC. In some embodiments, the individual has Stage T1, T2, T3, or T4 HCC according to AJCC (American Joint Commission on Cancer) staging criteria. In some embodiments, the individual is HBsAg positive. In some embodiments, the individual is HBsAg negative. In some embodiments, the individual has underlying liver cirrhosis. In some embodiments, the individual does not have the underlying liver cirrhosis. In some embodiments, the individual has a single lesion at presentation. In some embodiments, the individual has multiple lesions at presentation. In some embodiments, the individual is resistant to treatment of HCC with other agents (such as a non-nanoparticle formulation of a taxane, e.g., Taxol® or Taxotere®. In some embodiments, the individual is initially responsive to treatment of HCC with other agents (such as a non-nanoparticle formulation of a taxane, e.g., Taxol® or Taxotere® but has progressed after treatment.

Thus, for example, in some embodiments, there is provided a method of treating HCC in an individual (e.g., human) wherein the individual is HBsAg positive, comprising administering to the individual an effective amount of a composition comprising nanoparticles comprising a taxane and an albumin (such as human serum albumin). In some embodiments, there is provided a method of treating HCC in an individual (e.g., human) wherein the individual is HBsAg positive, comprising administering to the individual an effective amount of a composition comprising nanoparticles comprising a taxane and an albumin (such as human serum albumin), wherein the taxane in the nanoparticles is coated with the albumin. In some embodiments, there is provided a method of treating HCC in an individual (e.g., human) wherein the individual is HBsAg positive, comprising administering to the individual an effective amount of a composition comprising nanoparticles comprising paclitaxel and an albumin (such as human serum albumin). In some embodiments, there is provided a method of treating HCC in an individual (e.g., human) wherein the individual is HBsAg positive, comprising administering to the individual an effective amount of a composition comprising nanoparticles comprising paclitaxel and an albumin (such as human serum albumin), wherein the paclitaxel in the nanoparticles is coated with the albumin.

In some embodiments, there is provided a method of treating HCC in an individual (e.g., human) wherein the individual is HBsAg positive, comprising administering to the individual an effective amount of a composition comprising nanoparticles comprising a taxane and an albumin (such as human serum albumin), wherein the average particle size of the nanoparticles in the composition is no greater than about 200 nm (such as less than about 200 nm). In some embodiments, there is provided a method of treating HCC in an individual (e.g., human) wherein the individual is HBsAg positive, comprising administering to the individual an effective amount of a composition comprising nanoparticles comprising paclitaxel and an albumin (such as human serum albumin), wherein the average particle size of the nanoparticles in the composition is no greater than about 200 nm (such as less than about 200 nm).

In some embodiments, there is provided a method of treating HCC in an individual (e.g., human) wherein the individual is HBsAg positive, comprising administering to the individual an effective amount of a composition comprising nanoparticles comprising a taxane and an albumin (such as human serum albumin), wherein the taxane in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human) wherein the individual is HBsAg positive, comprising administering to the individual an effective amount of a composition comprising nanoparticles comprising paclitaxel and an albumin (such as human serum albumin), wherein the paclitaxel in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human) wherein the individual is HBsAg positive, comprising administering to the individual an effective amount of a composition comprising Nab-paclitaxel. In some embodiments, there is provided a method of treating HCC in an individual (e.g., human) wherein the individual is HBsAg positive, comprising administering to the individual an effective amount of Nab-paclitaxel.

In some embodiments, there is provided a method of treating HCC in an individual (e.g., human) wherein the individual is HBsAg negative, comprising administering to the individual an effective amount of a composition comprising nanoparticles comprising a taxane and an albumin (such as human serum albumin). In some embodiments, there is provided a method of treating HCC in an individual (e.g., human) wherein the individual is HBsAg negative, comprising administering to the individual an effective amount of a composition comprising nanoparticles comprising a taxane and an albumin (such as human serum albumin), wherein the taxane in the nanoparticles is coated with the albumin. In some embodiments, there is provided a method of treating HCC in an individual (e.g., human) wherein the individual is HBsAg negative, comprising administering to the individual an effective amount of a composition comprising nanoparticles comprising paclitaxel and an albumin (such as human serum albumin). In some embodiments, there is provided a method of treating HCC in an individual (e.g., human) wherein the individual is HBsAg negative, comprising administering to the individual an effective amount of a composition comprising nanoparticles comprising paclitaxel and an albumin (such as human serum albumin), wherein the paclitaxel in the nanoparticles is coated with the albumin.

In some embodiments, there is provided a method of treating HCC in an individual (e.g., human) wherein the individual is HBsAg negative, comprising administering to the individual an effective amount of a composition comprising nanoparticles comprising a taxane and an albumin (such as human serum albumin), wherein the average particle size of the nanoparticles in the composition is no greater than about 200 nm (such as less than about 200 nm). In some embodiments, there is provided a method of treating HCC in an individual (e.g., human) wherein the individual is HBsAg negative, comprising administering to the individual an effective amount of a composition comprising nanoparticles comprising paclitaxel and an albumin (such as human serum albumin), wherein the average particle size of the nanoparticles in the composition is no greater than about 200 nm (such as less than about 200 nm).

In some embodiments, there is provided a method of treating HCC in an individual (e.g., human) wherein the individual is HBsAg negative, comprising administering to the individual an effective amount of a composition comprising nanoparticles comprising a taxane and an albumin (such as human serum albumin), wherein the taxane in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human) wherein the individual is HBsAg negative, comprising administering to the individual an effective amount of a composition comprising nanoparticles comprising paclitaxel and an albumin (such as human serum albumin), wherein the paclitaxel in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human) wherein the individual is HBsAg negative, comprising administering to the individual an effective amount of a composition comprising Nab-paclitaxel. In some embodiments, there is provided a method of treating HCC in an individual (e.g., human) wherein the individual is HBsAg negative, comprising administering to the individual an effective amount of Nab-paclitaxel.

In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising a taxane and an albumin (such as human serum albumin). In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising a taxane and an albumin (such as human serum albumin), wherein the taxane in the nanoparticles is coated with the albumin. In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising paclitaxel and an albumin (such as human serum albumin). In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising paclitaxel and an albumin (such as human serum albumin), wherein the paclitaxel in the nanoparticles is coated with the albumin.

In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising a taxane and an albumin (such as human serum albumin), wherein the average particle size of the nanoparticles in the composition is no greater than about 200 nm (such as less than about 200 nm). In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising paclitaxel and an albumin (such as human serum albumin), wherein the average particle size of the nanoparticles in the composition is no greater than about 200 nm (such as less than about 200 nm).

In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising a taxane and an albumin (such as human serum albumin), wherein the taxane in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising nanoparticles comprising paclitaxel and an albumin (such as human serum albumin), wherein the paclitaxel in the nanoparticles is coated with the albumin, and wherein the average particle size of the nanoparticles in the composition is no greater than about 200 nm (such as less than about 200 nm). In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of a composition comprising Nab-paclitaxel. In some embodiments, there is provided a method of treating HCC in an individual (e.g., human) wherein the individual is resistant to treatment with other agents (such as a non-nanoparticle formulation of taxane, for example Taxol® or Taxotere®, comprising administering to the individual an effective amount of Nab-paclitaxel.

In some embodiments, the individual is a human who exhibits one or more symptoms associated with HCC. In some embodiments, the individual is at an early stage of HCC. In some embodiments, the individual is at an advanced stage of HCC. In some of embodiments, the individual is genetically or otherwise predisposed (e.g., having a risk factor) to developing HCC. These risk factors include, but are not limited to, age, sex, race, diet, history of previous disease, presence of precursor disease (e.g., hepatitis B or hepatitis C viral infection, liver cirrhosis), genetic (e.g., hereditary) considerations, and environmental exposure. In some embodiments, the individuals at risk for HCC include, e.g., those having relatives who have experienced HCC, and those whose risk is determined by analysis of genetic or biochemical markers. In some embodiments, the individual is positive for SPARC expression (for example based on IHC standard). In some embodiments, the individual is negative for SPARC expression.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy.

The methods described herein are useful for various aspects of HCC treatment. In some embodiments, there is provided a method of inhibiting HCC cell proliferation (such as HCC tumor growth) in an individual, comprising administering to the individual an effective amount of a composition comprising nanoparticles comprising a taxane and an albumin. In some embodiments, at least about 10% (including for example at least about any of 20%, 30%, 40%, 60%, 70%, 80%, 90%, or 100%) cell proliferation is inhibited. In some embodiments, the taxane is paclitaxel. In some embodiments, the taxane in the nanoparticle in the composition is administered by intravenous administration. In some embodiments, the taxane in the nanoparticle in the composition is administered by hepatic arterial infusion.

In some embodiments, there is provided a method of inhibiting HCC tumor metastasis in an individual, comprising administering to the individual an effective amount of a composition comprising nanoparticles comprising a taxane and an albumin. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided. In some embodiments, method of inhibiting metastasis to the lung is provided. In some embodiments, the taxane is paclitaxel. In some embodiments, the taxane in the nanoparticle in the composition is administered by intravenous administration. In some embodiments, the taxane in the nanoparticle in the composition is administered by hepatic arterial infusion.

In some embodiments, there is provided a method of reducing (such as eradiating) pre-existing HCC tumor metastasis (such as pulmonary metastasis or metastasis to the lymph node) in an individual, comprising administering to the individual an effective amount of a composition comprising nanoparticles comprising a taxane and an albumin. In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, method of reducing metastasis to the lung is provided. In some embodiments, the taxane is paclitaxel. In some embodiments, the taxane in the nanoparticle in the composition is administered by intravenous administration. In some embodiments, the taxane in the nanoparticle in the composition is administered by hepatic arterial infusion.

In some embodiments, there is provided a method of reducing incidence or burden of preexisting HCC tumor metastasis (such as pulmonary metastasis or metastasis to the lymph node) in an individual, comprising administering to the individual an effective amount of a composition comprising nanoparticles comprising a taxane and an albumin. In some embodiments, the taxane is paclitaxel. In some embodiments, the taxane in the nanoparticle in the composition is administered by intravenous administration. In some embodiments, the taxane in the nanoparticle in the composition is administered by hepatic arterial infusion.

In some embodiments, there is provided a method of reducing HCC tumor size in an individual, comprising administering to the individual an effective amount of a composition comprising nanoparticles comprising a taxane and an albumin. In some embodiments, the tumor size is reduced at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the taxane in the nanoparticle in the composition is administered by hepatic arterial infusion.

In some embodiments, there is provided a method of prolonging time to disease progression of HCC in an individual, comprising administering to the individual an effective amount of a composition comprising nanoparticles comprising a taxane and an albumin. In some embodiments, the method prolongs the time to disease progression by at least any of 1, 2, 3, 4, 5, 6, 7, 8, 9, 10, 11, or 12 weeks. In some embodiments, the taxane is paclitaxel. In some embodiments, the taxane in the nanoparticle in the composition is administered by intravenous administration. In some embodiments, the taxane in the nanoparticle in the composition is administered by hepatic arterial infusion.

In some embodiments, there is provided a method of prolonging survival of an individual having HCC, comprising administering to the individual an effective amount of a composition comprising nanoparticles comprising a taxane and an albumin. In some embodiments, the method prolongs the survival of the individual by at least any of 1, 2, 3, 4, 5, 6, 7, 8, 9, 10, 11, 12, 18, or 24 month. In some embodiments, the taxane is paclitaxel. In some embodiments, the taxane in the nanoparticle in the composition is administered by intravenous administration. In some embodiments, the taxane in the nanoparticle in the composition is administered by hepatic arterial infusion.

In some embodiments, there is provided a method of alleviating one or more symptoms in an individual having HCC, comprising administering to the individual an effective amount of a composition comprising nanoparticles comprising a taxane and an albumin. In some embodiments, the taxane in the nanoparticle in the composition is administered by intravenous administration. In some embodiments, the taxane in the nanoparticle in the composition is administered by hepatic arterial infusion.

It is understood that any of the embodiments described in this section apply to the embodiments provided in the section "methods of combination therapy." For example, in some embodiments, there is provided a method of alleviating one of more symptoms in an individual having HCC, comprising administering to the individual: a) an effective amount of a composition comprising nanoparticles comprising a taxane and an albumin, and b) an effective amount of an inhibitor of STMN1, wherein the nanoparticle composition and the STMN1 inhibitor are administered concurrently. In some embodiments, there is provided a method of a method of alleviating one or more symptoms in an individual having HCC, comprising administering to the individual: a) an effective amount of nanoparticles comprising paclitaxel coated with albumin (such as Abraxane®, and b) an effective amount of a an inhibitor of STMN1, wherein the nanoparticle composition and the STMN1 inhibitor are administered concurrently.

In some embodiments, there is provided a method of reducing (such as eradiating) pre-existing HCC tumor metastasis (such as pulmonary metastasis or metastasis to the lymph node) in an individual, comprising administering to the individual: a) an effective amount of a composition comprising nanoparticles comprising a taxane and an albumin, and b) an effective amount of an inhibitor of STMN1, wherein the nanoparticle composition and the STMN1 inhibitor are administered concurrently. In some embodiments, there is provided a method of reducing (such as eradiating) pre-existing HCC tumor metastasis (such as pulmonary metastasis or metastasis to the lymph node) in an individual, comprising administering to the individual: a) an effective amount of nanoparticles comprising paclitaxel coated with albumin (such as Abraxane®, and b) an effective amount of a an inhibitor of STMN1, wherein the nanoparticle composition and the STMN1 inhibitor are administered concurrently.

Methods of Combination Therapy

The methods of administering the composition comprising nanoparticles comprising a taxane and an albumin in some embodiments are carried out in conjunction with the administration of at least one other agent.

In some embodiments, there is provided a method of treating HCC in an individual in need thereof, comprising administering to the individual (a) an effective amount of a composition comprising nanoparticles comprising a taxane (such as paclitaxel) and albumin; and (b) an effective amount of at least one other agent, wherein said other agent inhibits microtubule disassembly. In some embodiments, there is provided a method of treating HCC in an individual in need thereof, comprising administering to the individual (a) an effective amount of a composition comprising nanoparticles comprising a taxane (such as paclitaxel) and albumin, wherein the taxane in the nanoparticles is coated with the albumin; and (b) an effective amount of at least one other agent, wherein said other agent inhibits microtubule disassembly. In some embodiments, there is provided a method of treating HCC in an individual in need thereof, comprising administering to the individual (a) an effective amount of a composition comprising nanoparticles comprising a taxane (such as paclitaxel) and albumin, wherein the average particle size of the nanoparticles in the nanoparticle composition is no greater than about 200 nm (such as less than about 200 nm); and (b) an effective amount of at least one other agent, wherein said other agent inhibits microtubule disassembly. In some embodiments, there is provided a method of treating HCC in an individual in need thereof, comprising administering to the individual (a) an effective amount of a composition comprising nanoparticles comprising a taxane (such as paclitaxel) and albumin, wherein the taxane in the nanoparticles is coated with the albumin, and wherein the average particle size of the nanoparticles in the nanoparticle composition is no greater than about 200 nm (such as less than about 200 nm); and (b) an effective amount of at least one other agent, wherein said other agent inhibits microtubule disassembly. In some embodiments, there is provided a method of treating HCC in an individual in need thereof, comprising administering to the individual (a) an effective amount of a composition comprising nanoparticles comprising Nab-paclitaxel (Abraxane®); and (b) an effective amount of at least one other agent, wherein said other agent inhibits microtubule disassembly. In some embodiments, there is provided a method of treating HCC in an individual in need thereof, comprising administering to the individual (a) an effective amount of Nab-paclitaxel (Abraxane®); and (b) an effective amount of at least one other agent, wherein said other agent inhibits microtubule disassembly. In some embodiments, the nanoparticle composition and the agent that inhibits microtubule disassembly are administered concurrently.

In some embodiments, the nanoparticle composition and the other agent have synergistic effect on treating HCC. In some embodiments, the other agent sensitizes the HCC cells to the treatment with the nanoparticle composition. In some embodiments, the other agent inhibits a molecule that promotes microtubule disassembly directly or indirectly. In some embodiments, the other agent inhibits the activity of the molecule that promotes microtubule disassembly. In some embodiments, the agent inhibits the expression of the molecule that promotes microtubule assembly. In some embodiments, the other agent inhibits a molecule selected from the group consisting of ABP1, ARHGAP4, HSPA8, LCP1, PACSIN2, RUNX1T1, STMN1, Tubulin, and TUBB4.

In some embodiments, the other agent activates a molecule that promotes microtubule assembly directly or indirectly. In some embodiments, the other agent enhances the activity of the molecule that promotes microtubule assembly. In some embodiments, the agent increases the expression of the molecule that promotes microtubule assembly. In some embodiments, the other agent activates a molecule selected from the group consisting of ABI1, BCL2L11, CDC42, CHRM3, CNN3, CSMD1, DDOST, DOCK7, EHMT2, ENAH, ERMAP, ERLF1, HDAC5, LDLRAP1, MCF2, OLA1, RASA1, SHC2, STMN2, and TRIP10.

In some embodiments, the other agent inhibits STMN1. STMN1 (Stathmin 1) is a microtubule-destabilizing phosphoprotein involved in the construction and function of the mitotic spindle. Rana et al., Expert Rev. Anticancer The. 8(9), 1461-1470 (2008). In some embodiments, there is provided a method of treating HCC in an individual in need thereof, comprising administering to the individual (a) an effective amount of a composition comprising nanoparticles comprising a taxane and albumin; and (b) an effective amount of an agent that inhibits STMN1. In some embodiments, the agent inhibits the activity of STMN1. In some embodiments, the agent inhibits the binding of STMN1 to tubulin. In some embodiments, the agent increases phosphorylation of STMN1. In some embodiments, the agent is an antibody against STMN1.

In some embodiments, there is provided a method of treating HCC in an individual in need thereof, comprising administering to the individual (a) an effective amount of a composition comprising nanoparticles comprising a taxane (such as paclitaxel) and albumin; and (b) an effective amount of an inhibitor of STMN1. In some embodiments, there is provided a method of treating HCC in an individual in need thereof, comprising administering to the individual (a) an effective amount of a composition comprising nanoparticles comprising a taxane (such as paclitaxel) and albumin, wherein the taxane in the nanoparticles is coated with the albumin; and (b) an effective amount of an inhibitor of STMN1. In some embodiments, there is provided a method of treating HCC in an individual in need thereof, comprising administering to the individual (a) an effective amount of a composition comprising nanoparticles comprising a taxane (such as paclitaxel) and albumin, wherein the average particle size of the nanoparticles in the nanoparticle composition is no greater than about 200 nm (such as less than about 200 nm); and (b) an effective amount of an inhibitor of STMN1. In some embodiments, there is provided a method of treating HCC in an individual in need thereof, comprising administering to the individual (a) an effective amount of a composition comprising nanoparticles comprising a taxane (such as paclitaxel) and albumin, wherein the taxane in the nanoparticles is coated with the albumin, and wherein the average particle size of the nanoparticles in the nanoparticle composition is no greater than about 200 nm (such as less than about 200 nm); and (b) an effective amount of an inhibitor of STMN1. In some embodiments, there is provided a method of treating HCC in an individual in need thereof, comprising administering to the individual (a) an effective amount of a composition comprising nanoparticles comprising Nab-paclitaxel (Abraxane®); and (b) an effective amount of an inhibitor of STMN1. In some embodiments, there is provided a method of treating HCC in an individual in need thereof, comprising administering to the individual (a) an effective amount of Nab-paclitaxel (Abraxane®); and (b) an effective amount of an inhibitor of STMN1. In some embodiments, the nanoparticle composition and the inhibitor of STMN1 are administered concurrently.

In some embodiments, the agent is a molecule of the Xanthone family. In some embodiments, the agent is a gemboge or a derivative thereof. Gamboge and derivatives include, for example, gambogic acid (GA) and gembogenic acid (GEA). Thus, for example, in some embodiments, there is provided a method of treating HCC in an individual, comprising administering to the individual a) an effective amount of a composition comprising nanoparticles comprising a taxane and an albumin, and b) an effective amount of a gamboge or a derivative thereof. In some embodiments, the invention provides a method of treating HCC in an individual, comprising administering to the individual a) an effective amount of a composition comprising nanoparticles comprising paclitaxel and an albumin (such as Nab-paclitaxel), and b) an effective amount of a gamboge or a derivative thereof. In some embodiments, the gamboge or the derivative thereof has synergistic effect when combining with the effective amount of the taxane nanoparticle composition in inhibiting cell proliferation or metastasis in HCC. In some embodiments, the gamboge or the derivative thereof sensitizes the HCC cells to the taxane nanoparticle composition (such as Nab-paclitaxel).

Thus, for example, in some embodiments, there is provided a method of treating HCC in an individual in need thereof, comprising administering to the individual (a) an effective amount of a composition comprising nanoparticles comprising a taxane (such as paclitaxel) and albumin; and (b) an effective amount of a gamboge or the derivative thereof. In some embodiments, there is provided a method of treating HCC in an individual in need thereof, comprising administering to the individual (a) an effective amount of a composition comprising nanoparticles comprising a taxane (such as paclitaxel) and albumin, wherein the taxane in the nanoparticles is coated with the albumin; and (b) an effective amount of a gamboge or the derivative thereof. In some embodiments, there is provided a method of treating HCC in an individual in need thereof, comprising administering to the individual (a) an effective amount of a composition comprising nanoparticles comprising a taxane (such as paclitaxel) and albumin, wherein the average particle size of the nanoparticles in the nanoparticle composition is no greater than about 200 nm (such as less than about 200 nm); and (b) an effective amount of a gamboge or the derivative thereof. In some embodiments, there is provided a method of treating HCC in an individual in need thereof, comprising administering to the individual (a) an effective amount of a composition comprising nanoparticles comprising a taxane (such as paclitaxel) and albumin, wherein the taxane in the nanoparticles is coated with the albumin, and wherein the average particle size of the nanoparticles in the nanoparticle composition is no greater than about 200 nm (such as less than about 200 nm); and (b) an effective amount of a gamboge or the derivative thereof. In some embodiments, there is provided a method of treating HCC in an individual in need thereof, comprising administering to the individual (a) an effective amount of a composition comprising nanoparticles comprising Nab-paclitaxel (Abraxane®); and (b) an effective amount of a gamboge or the derivative thereof. In some embodiments, there is provided a method of treating HCC in an individual in need thereof, comprising administering to the individual (a) an effective amount of Nab-paclitaxel (Abraxane®); and (b) an effective amount of a gamboge or the derivative thereof. In some embodiments, the nanoparticle composition and the gamboge or the derivative thereof are administered concurrently.

In some embodiments, the other agent inhibits the expression of STMN1. In some embodiments, the agent is an anti-STMN1 ribozyme (such as Rz184 and Rz305). In some embodiments, the STMN1 inhibitor is an antisense oligonucleotide that inhibits the expression of STMN1. In some embodiments, the antisense oligonucleotide is an antisense oligodeoxynucleotide. In some embodiments, the antisense oligonucleotide is an antisense oligodeoxyribonucleotide. In other embodiments, the STMN1 inhibitor is a small interfering RNA (siRNA). In some embodiments, the other agent is a composition that comprises more than one siRNA against STMN1. Suitable siRNAs against STMN1 are known in the art. For example, the STMN1 siGenomeSMART pool is a mixture of four siRNAs against STMN1.

Thus, for example, in some embodiments, there is provided a method of treating HCC in an individual in need thereof, comprising administering to the individual (a) an effective amount of a composition comprising nanoparticles comprising a taxane (such as paclitaxel) and albumin; and (b) an effective amount of an siRNA against STMN1. In some embodiments, there is provided a method of treating HCC in an individual in need thereof, comprising administering to the individual (a) an effective amount of a composition comprising nanoparticles comprising a taxane (such as paclitaxel)

and albumin, wherein the taxane in the nanoparticles is coated with the albumin; and (b) an effective amount of an siRNA against STMN1. In some embodiments, there is provided a method of treating HCC in an individual in need thereof, comprising administering to the individual (a) an effective amount of a composition comprising nanoparticles comprising a taxane (such as paclitaxel) and albumin, wherein the average particle size of the nanoparticles in the nanoparticle composition is no greater than about 200 nm (such as less than about 200 nm); and (b) an effective amount of an siRNA against STMN1. In some embodiments, there is provided a method of treating HCC in an individual in need thereof, comprising administering to the individual (a) an effective amount of a composition comprising nanoparticles comprising a taxane (such as paclitaxel) and albumin, wherein the taxane in the nanoparticles is coated with the albumin, and wherein the average particle size of the nanoparticles in the nanoparticle composition is no greater than about 200 nm (such as less than about 200 nm); and (b) an effective amount of an siRNA against STMN1. In some embodiments, there is provided a method of treating HCC in an individual in need thereof, comprising administering to the individual (a) an effective amount of a composition comprising nanoparticles comprising Nab-paclitaxel (Abraxane®); and (b) an effective amount of an siRNA against STMN1. In some embodiments, there is provided a method of treating HCC in an individual in need thereof, comprising administering to the individual (a) an effective amount of Nab-paclitaxel (Abraxane®); and (b) an effective amount of an siRNA against STMN1. In some embodiments, the nanoparticle composition and the siRNA against STMN1 are administered concurrently.

In some embodiments, there is provided a method of treating HCC in an individual in need thereof, comprising administering to the individual (a) an effective amount of a composition comprising nanoparticles comprising a taxane and albumin; and (b) an effective amount of another agent, wherein the other agent is an inhibitor of TUBB4. In some embodiments, the other agent inhibits the polymerization of TUBB4. In some embodiments, the other agent inhibits the expression of TUBB4. For example, in some embodiments, the TUBB4 inhibitor is an antisense oligonucleotide that inhibits the expression of TUBB4. In some embodiments, the TUBB4 inhibitor is an siRNA against TUBB4. In some embodiments, the effective amounts of the taxane nanoparticle composition and a TUBB4 inhibitor synergistically inhibit cell proliferation or metastasis in HCC. In some embodiments, the TUBB4 inhibitor sensitizes HCC cells to the taxane nanoparticle composition (such as Nab-paclitaxel).

In some embodiments, there is provided a method of treating HCC in an individual in need thereof, comprising administering to the individual (a) an effective amount of a composition comprising nanoparticles comprising a taxane and albumin; and (b) an effective amount of another agent, wherein the other agent is an activator of DOCK7.

The other agents described herein can be the agents themselves, pharmaceutically acceptable salts thereof, and pharmaceutically acceptable esters thereof, as well as stereoisomers, enantiomers, racemic mixtures, and the like. The other agent or agents as described can be administered as well as a pharmaceutical composition containing the agent(s), wherein the pharmaceutical composition comprises a pharmaceutically acceptable carrier vehicle, or the like.

In some embodiments, two or more chemotherapeutic agents are administered in addition to the taxane in the nanoparticle composition. These two or more chemotherapeutic agents may (but not necessarily) belong to different classes of chemotherapeutic agents. Examples of these combinations are provided herein. Other combinations are also contemplated.

Thus, for example, in some embodiments, there is provided a method of treating HCC in an individual, comprising administering to the individual a) an effective amount of a composition comprising nanoparticles comprising a taxane and an albumin, b) an effective amount of an siRNA against STMN1, and c) an effective amount of a gamboge and a derivative thereof. In some embodiments, there is provided a method of treating HCC in an individual, comprising administering to the individual a) an effective amount of a composition comprising nanoparticles comprising a taxane and an albumin, b) an effective amount of STMN1 inhibitor; and c) an effective amount of a TUBB4 inhibitor. In some embodiments, there is provided a method of treating HCC in an individual, comprising administering to the individual a) an effective amount of a composition comprising nanoparticles comprising a taxane and an albumin (e.g., human serum albumin), b) an effective amount of STMN1 inhibitor, and c) an effective amount of DOCK7 activator.

Also provided are pharmaceutical compositions comprising nanoparticles comprising a taxane and an albumin (such as human serum albumin) for use in any of the methods of treating HCC described herein.

It is understood that any of the methods of treating HCC described herein (such as above section "Methods of Treating HCC") apply to and include description of combination therapies. In some embodiments, a lower amount of each pharmaceutically active compound is used as part of a combination therapy compared to the amount generally used for individual therapy. In some embodiments, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. For example, the use of a small amount of pharmaceutically active compound may result in a reduction in the number, severity, frequency, or duration of one or more side-effects associated with the compound.

The dosing regimens for the methods described herein are further provided below.

Additional Exemplary Embodiments

The present application in some embodiments provides a method of treating hepatocellular carcinoma (HCC) in an individual in need thereof, comprising administering to the individual an effective amount of a composition comprising nanoparticles comprising a taxane and an albumin.

In some embodiments, there is provided a method of treating HCC in an individual in need thereof, comprising administering to the individual (a) an effective amount of a composition comprising nanoparticles comprising a taxane and albumin; and (b) an effective amount of at least one other agent, wherein said other agent inhibits microtubule disassembly. In some embodiments, the nanoparticle composition and the other agent are administered simultaneously or sequentially. In some embodiments, the nanoparticle composition and the other agent are administered concurrently. In some embodiments, the other agent inhibits a molecule that promotes microtubule disassembly directly or indirectly. In some embodiments, the other agent inhibits a molecule selected from the group consisting of ABP1, ARHGAP4, HSPA8, LCP1, PACSIN2, RUNX1T1, STMN1, and Tubulin, and TUBB4. In some embodiments, the other agent is an inhibitor of STMN1. In some embodiments, the other agent is an siRNA against STMN1. In some embodiments, the other agent is a gamboge or a derivative thereof. In some embodiments, the other agent activates a molecule that promotes microtubule assembly directly or indirectly. In some embodiments, the other agent activates a molecule selected from the group consisting of ABI1, BCL2L11, CDC42, CHRM3, CNN3, CSMD1, DDOST, DOCK7, EHMT2, ENAH, ERMAP, ERLF1, HDAC5, LDLRAP1, MCF2, OLA1, RASA1, SHC2, STMN2, and TRIP10.

In some embodiments according to any of the methods described above in this section, the HCC is liver cell carcinoma, fibrolamellar variant of HCC, or mixed hepatocellular cholangiocarcinoma.

In some embodiments according to any of the methods described above in this section, wherein the HCC is early stage HCC, non-metastatic HCC, primary HCC, advanced HCC, locally advanced HCC, metastatic HCC, HCC in remission, recurrent HCC, HCC in an adjuvant setting, or HCC in a neoadjuvant setting.

In some embodiments according to any of the methods described above in this section, wherein the composition comprising nanoparticles comprising a taxane and albumin is administered parenterally. In some embodiments, the composition comprising nanoparticles comprising a taxane and albumin is administered intravenously, intraarterially, intrahepatically, or intraportally.

In some embodiments according to any of the methods described above in this section, the taxane is paclitaxel.

In some embodiments according to any of the methods described above in this section, the nanoparticles in the composition have an average diameter of no greater than about 200 nm. In some embodiments, the nanoparticles in the composition have an average diameter of less than about 200 nm.

In some embodiments according to any of the methods described above in this section, wherein the taxane in the nanoparticles are coated with albumin.

In some embodiments according to any of the methods described above in this section, the individual is human.

Dosing and Method of Administering the Nanoparticle Compositions

The dose of the taxane nanoparticle compositions administered to an individual (such as a human) may vary with the particular composition, the mode of administration, and the type of HCC being treated. In some embodiments, the amount of the composition is effective to result in an objective response (such as a partial response or a complete response). In some embodiments, the amount of the taxane nanoparticle composition is sufficient to result in a complete response in the individual. In some embodiments, the amount of the taxane nanoparticle composition is sufficient to result in a partial response in the individual. In some embodiments, the amount of the taxane nanoparticle composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the taxane nanoparticle composition. Responses of an individual to the treatment of the methods described herein can be determined, for example, based on RECIST levels.

In some embodiments, the amount of the composition is sufficient to prolong progress-free survival of the individual. In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the taxane nanoparticle composition.

In some embodiments, the amount of the composition, first therapy, second therapy, or combination therapy is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of HCC cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the taxane (e.g., paclitaxel) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regime. In some embodiments, the amount of the composition is more than about any of 80%, 90%, 95%, or 98% of the MTD.

In some embodiments, the amount of a taxane (e.g., paclitaxel) in the composition is included in any of the following ranges: about 0.1 mg to about 500 mg, about 0.1 mg to about 2.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) in the effective amount of the composition (e.g., a unit dosage form) is in the range of about 5 mg to about 500 mg, such as about 30 mg to about 300 mg or about 50 mg to about 200 mg. In some embodiments, the concentration of the taxane (e.g., paclitaxel) in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the taxane (e.g., paclitaxel) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. In some embodiments, the concentration of the taxane (e.g., paclitaxel) is no more than about any of 100 mg/ml, 90 mg/ml, 80 mg/ml, 70 mg/ml, 60 mg/ml, 50 mg/ml, 40 mg/ml, 30 mg/ml, 20 mg/ml, 10 mg/ml, or 5 mg/ml.

Exemplary effective amounts of a taxane (e.g., paclitaxeL) in the nanoparticle composition include, but are not limited to, at least about any of 25 $mg/m^2$, 30 $mg/m^2$, 50 $mg/m^2$, 60 $mg/m^2$, 75 $mg/m^2$, 80 $mg/m^2$, 90 $mg/m^2$, 100 $mg/m^2$, 120 $mg/m^2$, 125 $mg/m^2$, 150 $mg/m^2$, 160 $mg/m^2$, 175 $mg/m^2$, 180 $mg/m^2$, 200 $mg/m^2$, 210 $mg/m^2$, 220 $mg/m^2$, 250 $mg/m^2$, 260 $mg/m^2$, 300 $mg/m^2$, 350 $mg/m^2$, 400 $mg/m^2$, 500 $mg/m^2$, 540 $mg/m^2$, 750 $mg/m^2$, 1000 $mg/m^2$, or 1080 $mg/m^2$ of a taxane (e.g., paclitaxel). In various embodiments, the composition includes less than about any of 350 mg/m², 300 mg/m², 250 mg/m², 200 mg/m², 150 mg/m², 120 mg/m², 100 mg/m², 90 mg/m², 50 mg/m², or 30 mg/m² of a taxane (e.g., paclitaxel). In some embodiments, the amount of the taxane (e.g., paclitaxel) per administration is less than about any of 25 mg/m², 22 mg/m², 20 mg/m², 18 mg/m², 15 mg/m², 14 mg/m², 13 mg/m², 12 mg/m², 11 mg/m², 10 mg/m², 9 mg/m², 8 mg/m², 7 mg/m², 6 mg/m², 5 mg/m², 4 mg/m², 3 mg/m², 2 mg/m², or 1 mg/m². In some embodiments, the effective amount of a taxane (e.g., paclitaxel) in the composition is included in any of the following ranges: about 1 to about 5 mg/m², about 5 to about 10 mg/m², about 10 to about 25 mg/m², about 25 to about 50 mg/m², about 50 to about 75 mg/m², about 75 to about 100 mg/m², about 100 to about 125 mg/m², about 125 to about 150 mg/m², about 150 to about 175 mg/m², about 175 to about 200 mg/m², about 200 to about 225 mg/m², about 225 to about 250 mg/m², about 250 to about 300 mg/m², about 300 to about 350 mg/m², or about 350 to about 400 mg/m². In some embodiments, the effective amount of a taxane (e.g., paclitaxel) in the composition is about 5 to about 300 mg/m², such as about 100 to about 150 mg/m², about 120 mg/m², about 130 mg/m², or about 140 mg/m².

In some embodiments of any of the above aspects, the effective amount of a taxane (e.g., paclitaxel) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of a taxane (e.g., paclitaxel) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a taxane (e.g., paclitaxel).

Exemplary dosing frequencies for the administration of the nanoparticle compositions include, but are not limited to, daily, every two days, every three days, every four days, every five days, every six days, weekly without break, three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, the taxane (e.g., paclitaxel) is administered over a period of at least ten days, wherein the interval between each administration is no more than about two days, and wherein the dose of the taxane (e.g., paclitaxel) at each administration is about 0.25 mg/m² to about 250 mg/m², about 0.25 mg/m² to about 150 mg/m², about 0.25 mg/m² to about 75 mg/m², such as about 0.25 mg/m² to about 25 mg/m², or about 25 mg/m² to about 50 mg/m².

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the dosage of a taxane (e.g., paclitaxel) in a nanoparticle composition can be in the range of 5-400 mg/m² when given on a 3 week schedule, or 5-250 mg/m² (such as 80-150 mg/m², for example 100-120 mg/m²) when given on a weekly schedule. For example, the amount of a taxane (e.g., paclitaxel) is about 60 to about 300 mg/m² (e.g., about 260 mg/m²) on a three week schedule.

Other exemplary dosing schedules for the administration of the nanoparticle composition (e.g., paclitaxel/albumin nanoparticle composition) include, but are not limited to, 100 mg/m², weekly, without break; 75 mg/m² weekly, 3 out of four weeks; 100 mg/m², weekly, 3 out of 4 weeks; 125 mg/m², weekly, 3 out of 4 weeks; 125 mg/m², weekly, 2 out of 3 weeks; 130 mg/m², weekly, without break; 175 mg/m², once every 2 weeks; 260 mg/m², once every 2 weeks; 260 mg/m², once every 3 weeks; 180-300 mg/m², every three weeks; 60-175 mg/m², weekly, without break; 20-150 mg/m² twice a week; and 150-250 mg/m² twice a week. The dosing frequency of the composition may be adjusted over the course of the treatment based on the judgment of the administering physician.

In some embodiments, the individual is treated for at least about any of one, two, three, four, five, six, seven, eight, nine, or ten treatment cycles.

The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

Other exemplary dose of the taxane (in some embodiments paclitaxel) in the nanoparticle composition include, but is not limited to, about any of 50 mg/m², 60 mg/m², 75 mg/m², 80 mg/m², 90 mg/m², 100 mg/m², 120 mg/m², 160 mg/m², 175 mg/m², 200 mg/m², 210 mg/m², 220 mg/m², 260 mg/m², and 300 mg/m². For example, the dosage of paclitaxel in a nanoparticle composition can be in the range of about 100-400 mg/m² when given on a 3 week schedule, or about 50-250 mg/m² when given on a weekly schedule.

The nanoparticle compositions can be administered to an individual (such as human) via various routes, including, for example, intravenous, intra-arterial, intraperitoneal, intrapulmonary, oral, inhalation, intravesicular, intramuscular, intratracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion.

Modes of Administration of Combination Therapies

The dosing regimens described in the section above apply to both monotherapy and combination therapy settings. The modes of administration for combination therapy methods are further described below.

In some embodiments, the nanoparticle composition and the other agent (including the specific chemotherapeutic agents described herein) are administered simultaneously. When the drugs are administered simultaneously, the drug in the nanoparticles and the other agent may be contained in the same composition (e.g., a composition comprising both the nanoparticles and the other agent) or in separate compositions (e.g., the nanoparticles are contained in one composition and the other agent is contained in another composition).

In some embodiments, the nanoparticle composition and the other agent are administered sequentially. Either the nanoparticle composition or the other agent may be administered first. The nanoparticle composition and the other agent are contained in separate compositions, which may be contained in the same or different packages.

In some embodiments, the administration of the nanoparticle composition and the other agent are concurrent, i.e., the administration period of the nanoparticle composition and that of the other agent overlap with each other. In some embodiments, the nanoparticle composition is administered for at least one cycle (for example, at least any of 2, 3, or 4 cycles) prior to the administration of the other agent. In some embodiments, the other agent is administered for at least any of one, two, three, or four weeks. In some embodiments, the administrations of the nanoparticle composition and the other agent are initiated at about the same time (for example, within any one of 1, 2, 3, 4, 5, 6, or 7 days). In some embodiments, the administration of the nanoparticle composition and the other agent are terminated at about the same time (for example, within any one of 1, 2, 3, 4, 5, 6, or 7 days). In some embodiments, the administration of the other agent continues (for example for about any one of 1, 2, 3, 4, 5, 6, 7, 8, 9, 10, 11, or 12 months) after the termination of the administration of the nanoparticle composition. In some embodiments, the administration of the other agent is initiated after (for example after about any one of 1, 2, 3, 4, 5, 6, 7, 8, 9, 10, 11, or 12 months) the initiation of the administration of the nanoparticle composition. In some embodiments, the administrations of the nanoparticle composition and the other agent are initiated and terminated at about the same time. In some embodiments, the administrations of the nanoparticle composition and the other agent are initiated at about the same time and the administration of the other agent continues (for example for about any one of 1, 2, 3, 4, 5, 6, 7, 8, 9, 10, 11, or 12 months) after the termination of the administration of the nanoparticle composition. In some embodiments, the administration of the nanoparticle composition and the other agent stop at about the same time and the administration of the other agent is initiated after (for example after about any one of 1, 2, 3, 4, 5, 6, 7, 8, 9, 10, 11, or 12 months) the initiation of the administration of the nanoparticle composition. In some embodiments, the method comprises more than one treatment cycles, wherein at least one of the treatment cycles comprise the administration of (a) an effective amount of a composition comprising nanoparticles comprising a taxane (such as paclitaxel) and albumin; and (b) an effective amount of at least one other agent, wherein said other agent inhibits microtubule disassembly. In some embodiments, the treatment cycle comprises no less than about (such as about) 21 days. In some embodiments, the treatment cycle comprises less than about 21 days (for example weekly or daily).

In some embodiments, the administration of the nanoparticle composition and the other agent are non-concurrent. For example, in some embodiments, the administration of the nanoparticle composition is terminated before the other agent is administered. In some embodiments, the administration of the other agent is terminated before the nanoparticle composition is administered. The time period between these two non-concurrent administrations can range from about two to eight weeks, such as about four weeks.

The dosing frequency of the drug-containing nanoparticle composition and the other agent may be adjusted over the course of the treatment, based on the judgment of the administering physician. When administered separately, the drug-containing nanoparticle composition and the other agent can be administered at different dosing frequency or intervals. For example, the drug-containing nanoparticle composition can be administered weekly, while a chemotherapeutic agent can be administered more or less frequently. In some embodiments, sustained continuous release formulation of the drug-containing nanoparticle and/or chemotherapeutic agent may be used. Various formulations and devices for achieving sustained release are known in the art. A combination of the administration configurations described herein can also be used.

The nanoparticle composition and the other agent can be administered using the same route of administration or different routes of administration. In some embodiments (for both simultaneous and sequential administrations), the taxane in the nanoparticle composition and the other agent are administered at a predetermined ratio. For example, in some embodiments, the ratio by weight of the taxane in the nanoparticle composition and the other agent is about 1 to 1. In some embodiments, the weight ratio may be between about 0.001 to about 1 and about 1000 to about 1, or between about 0.01 to about 1 and 100 to about 1. In some embodiments, the ratio by weight of the taxane in the nanoparticle composition and the other agent is less than about any of 100:1, 50:1, 30:1, 10:1, 9:1, 8:1, 7:1, 6:1, 5:1, 4:1, 3:1, 2:1, and 1:1. In some embodiments, the ratio by weight of the taxane in the nanoparticle composition and the other agent is more than about any of 1:1, 2:1, 3:1, 4:1, 5:1, 6:1, 7:1, 8:1, 9:1, 30:1, 50:1, 100:1. Other ratios are contemplated.

The doses required for the taxane and/or the other agent may (but not necessarily) be lower than what is normally required when each agent is administered alone. Thus, in some embodiments, a subtherapeutic amount of the drug in the nanoparticle composition and/or the other agent is administered. "Subtherapeutic amount" or "subtherapeutic level" refer to an amount that is less than the therapeutic amount, that is, less than the amount normally used when the drug in the nanoparticle composition and/or the other agent are administered alone. The reduction may be reflected in terms of the amount administered at a given administration and/or the amount administered over a given period of time (reduced frequency).

In some embodiments, enough chemotherapeutic agent is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough drug in the nanoparticle composition is administered so as to allow reduction of the normal dose of the other agent required to effect the same degree of treatment by at least about any of 5%, 10%, 20%, 30%, 50%, 60%, 70%, 80%, 90%, or more.

In some embodiments, the dose of both the taxane in the nanoparticle composition and the other agent are reduced as compared to the corresponding normal dose of each when administered alone. In some embodiments, both the taxane in the nanoparticle composition and the other agent are administered at a subtherapeutic, i.e., reduced, level. In some embodiments, the dose of the nanoparticle composition and/or the other agent is substantially less than the established maximum toxic dose (MTD). For example, the dose of the nanoparticle composition and/or the other agent is less than about 50%, 40%, 30%, 20%, or 10% of the MTD.

A combination of the administration configurations described herein can be used. The combination therapy methods described herein may be performed alone or in conjunction with another therapy, such as chemotherapy, radiation therapy, surgery, hormone therapy, gene therapy, immunotherapy, chemoimmunotherapy, hepatic artery-based therapy, cryotherapy, ultrasound therapy, liver transplantation, local ablative therapy, radiofrequency ablation therapy, photodynamic therapy, and the like. Additionally, a person having a greater risk of developing the HCC may receive treatments to inhibit or and/or delay the development of the disease.

The other agent described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. In some embodiments, the other agent is administrated intravenously. In some embodiments, the nanoparticle composition is administered orally.

The dosing frequency of the other agent can be the same or different from that of the nanoparticle composition. Exemplary frequencies are provided above. As further example, the other agent can be administered three times a day, two times a day, daily, 6 times a week, 5 times a week, 4 times a week, 3 times a week, two times a week, weekly. In some embodiments, the other agent is administered twice daily or three times daily. Exemplary amounts of the other agent include, but are not limited to, any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. For example, the other agent can be administered at a dose of about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). For example, in some embodiments, STMN1 inhibitor is administered at about 1-100 mg/kg (including for example 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg), every two days for five times.

In some embodiments, the effective amount of taxane in the nanoparticle composition is between about 45 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 300 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 150 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 150 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the nanoparticle composition is about 100 mg/m$^2$. In some embodiments, the effective amount of taxane in the nanoparticle composition is between about 170 mg/m$^2$ to about 200 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 200 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the nanoparticle composition is about 260 mg/m$^2$. In some embodiments of any of the above methods, the effective amount of the other agent is about 20-30 mg/kg, about 30-40 mg/kg, about 40-50 mg/kg, about 50-60 mg/kg, about 60-70 mg/kg, about 70-80 mg/kg, about 80-100 mg/kg, or about 100-120 mg/kg.

In some embodiments, the appropriate doses of other agents are approximately those already employed in clinical therapies wherein the other agent is administered alone or in combination with other agents.

Nanoparticle Compositions

The nanoparticle compositions described herein comprise nanoparticles comprising (in various embodiments consisting essentially of) a taxane (such as paclitaxel) and an albumin (such as human serum albumin). Nanoparticles of poorly water soluble drugs (such as taxane) have been disclosed in, for example, U.S. Pat. Nos. 5,916,596; 6,506,405; 6,749,868, 6,537,579, 7,820,788, and also in U.S. Pat. Pub. Nos. 2006/0263434, and 2007/0082838; PCT Patent Application WO08/137,148, each of which is incorporated by reference in their entirety.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 to about 400 nm, including for example about 20 to about 200 nm, about 40 to about 200 nm, about 30 to about 180 nm, and any one of about 40 to about 150, about 50 to about 120, and about 60 to about 100 nm.

In some embodiments, the albumin has sulfhydral groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprise the taxane (such as paclitaxel) coated with an albumin (e.g., human serum albumin). In some embodiments, the composition comprises a taxane in both nanoparticle and non-nanoparticle forms (e.g., in the form of paclitaxel solutions or in the form of soluble albumin/nanoparticle complexes), wherein at least about any one of 50%, 60%, 70%, 80%, 90%, 95%, or 99% of the taxane in the composition are in nanoparticle form. In some embodiments, the taxane in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of a taxane that is substantially free of polymeric materials (such as polymeric matrix).

In some embodiments, the composition comprises albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of albumin (such as human serum albumin) and a taxane in the nanoparticle composition is about 18:1 or less, such as about 15:1 or less, for example about 10:1 or less. In some embodiments, the weight ratio of albumin (such as human serum albumin) and taxane in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of albumin and taxane in the nanoparticle portion of the composition is about any one of 1:2, 1:3, 1:4, 1:5, 1:10, 1:15, or less. In some embodiments, the weight ratio of the albumin (such as human serum albumin) and the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., *The Pharmacological Basis of Therapeutics*, $9^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15

(199b), and Carter et al., *Adv. Protein. Chem.*, 45, 153-203 (1994)). Paclitaxel and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Gamido et al., *Rev. Esp. Anestestiol. Reanim.*, 41, 308-12 (1994)). In addition, docetaxel has been shown to bind to human plasma proteins (see, e.g., Urien et al., *Invest. New Drugs,* 14(b), 147-51 (1996)).

The albumin (such as human serum albumin) in the composition generally serves as a carrier for the taxane, i.e., the albumin in the composition makes the taxane more readily suspendable in an aqueous medium or helps maintain the suspension as compared to compositions not comprising an albumin. This can avoid the use of toxic solvents (or surfactants) for solubilizing the taxane, and thereby can reduce one or more side effects of administration of the taxane into an individual (such as a human). Thus, in some embodiments, the composition described herein is substantially free (such as free) of surfactants, such as Cremophor (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant.

The amount of albumin in the composition described herein will vary depending on other components in the composition. In some embodiments, the composition comprises an albumin in an amount that is sufficient to stabilize the taxane in an aqueous suspension, for example, in the form of a stable colloidal suspension (such as a stable suspension of nanoparticles). In some embodiments, the albumin is in an amount that reduces the sedimentation rate of the taxane in an aqueous medium. For particle-containing compositions, the amount of the albumin also depends on the size and density of nanoparticles of the taxane.

A taxane is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize the taxane in an aqueous suspension at a certain concentration. For example, the concentration of the taxane in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the taxane is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of albumin. In some embodiments, the composition, in liquid form, comprises about 0.5% to about 5% (w/v) of albumin.

In some embodiments, the weight ratio of albumin, e.g., albumin, to the taxane in the nanoparticle composition is such that a sufficient amount of taxane binds to, or is transported by, the cell. While the weight ratio of albumin to taxane will have to be optimized for different albumin and taxane combinations, generally the weight ratio of albumin, e.g., albumin, to taxane (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to taxane weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human serum albumin) to the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the albumin allows the composition to be administered to an individual (such as human) without significant side effects. In some embodiments, the albumin (such as human serum albumin) is in an amount that is effective to reduce one or more side effects of administration of the taxane to a human. The term "reducing one or more side effects of administration of the taxane" refers to reduction, alleviation, elimination, or avoidance of one or more undesirable effects caused by the taxane, as well as side effects caused by delivery vehicles (such as solvents that render the taxanes suitable for injection) used to deliver the taxane. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with taxanes can be reduced.

In some embodiments, the nanoparticle composition comprises Abraxane® (Nab-paclitaxel). In some embodiments, the nanoparticle composition is Abraxane® (Nab-paclitaxel). Abraxane® is a formulation of paclitaxel stabilized by human albumin USP, which can be dispersed in directly injectable physiological solution. When dispersed in a suitable aqueous medium such as 0.9% sodium chloride injection or 5% dextrose injection, Abraxane® forms a stable colloidal suspension of paclitaxel. The mean particle size of the nanoparticles in the colloidal suspension is about 130 nanometers. Since HSA is freely soluble in water, Abraxane® can be reconstituted in a wide range of concentrations ranging from dilute (0.1 mg/ml paclitaxel) to concentrated (20 mg/ml paclitaxel), including for example about 2 mg/ml to about 8 mg/ml, or about 5 mg/ml.

Methods of making nanoparticle compositions are known in the art. For example, nanoparticles containing taxanes (such as paclitaxel) and albumin (such as human serum albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579 and 7,820,788 and also in U.S. Pat. Pub. Nos. 2007/0082838, 2006/0263434 and PCT Application WO08/137,148.

Briefly, the taxane (such as paclitaxel) is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

Other Components in the Nanoparticle Compositions

The nanoparticles described herein can be present in a composition that include other agents, excipients, or stabilizers. For example, to increase stability by increasing the negative zeta potential of nanoparticles, one or more of negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596, 6,096,331, and 7,820,788). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits, Medicines, and Compositions

The invention also provides kits, medicines, compositions, and unit dosage forms for use in any of the methods described herein.

Kits of the invention include one or more containers comprising taxane-containing nanoparticle compositions (or unit dosage forms and/or articles of manufacture) and/or another agent (such as the agents described herein), and in some embodiments, further comprise instructions for use in accordance with any of the methods described herein. The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a composition comprising nanoparticles comprising a taxane and an albumin (such as human serum albumin), and b) instructions for administering the nanoparticle composition for treatment of HCC. In some embodiments, the kit comprises a) a composition comprising nanoparticles comprising a taxane and an albumin (such as human serum albumin), b) an effective amount of at least one other agent, wherein the other agent inhibits microtubule disassembly. In some embodiments, the kit comprises a) a composition comprising nanoparticles comprising a taxane and an albumin (such as human serum albumin), and b) instructions for administering the nanoparticle composition for treatment of HCC. In some embodiments, the kit comprises a) a composition comprising nanoparticles comprising a taxane and an albumin (such as human serum albumin), b) an effective amount of at least one other agent, wherein the other agent inhibits microtubule disassembly, and c) instructions for administering the nanoparticle composition and the other agents for treatment of HCC. The nanoparticles and the other agents can be present in separate containers or in a single container. For example, the kit may comprise one distinct composition or two or more compositions wherein one composition comprises nanoparticles and one composition comprises another agent.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the nanoparticle compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the taxane (such as taxane) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the taxane and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition) for use in treating HCC, comprising nanoparticles comprising a taxane and an albumin (such as human serum albumin). In some embodiments, there is provided a medicine (or composition or a unit dosage form) for use in treating HCC in conjunction with another agent, comprising nanoparticles comprising a taxane and an albumin (such as human serum albumin), wherein the other agent inhibits microtubule disassembly. In some embodiments, there is provided a medicine (or composition or a unit dosage form) for use in treating HCC, comprising nanoparticles comprising a taxane and an albumin (such as human serum albumin) and at least one other agent, wherein the other agent inhibits microtubule disassembly.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Evaluation of Efficacy of Nanoparticle (Nab-Paclitaxel) in In Vitro and In Vivo Hepatocellular Carcinoma (HCC) Models This example demonstrates the activity of Nab-paclitaxel in in vitro and in vivo HCC models.

Materials and Methods

Expression Profiling and Informatic Analysis

Gene expression profiling on 43 paired HCC tumors and adjacent non-tumoral livers was performed according to method described by Wong N. et al., *Clinical Cancer Research* 11:1319-26 (2005). Demographic information of cases studied is shown in Table 1. Normal liver RNA from three individuals were pooled and used as reference control in array hybridisation (Ambion, Austin, Tex.; Clontech Laboratory Inc., Palo Alto, Calif.; and Strategene, La Jolla, Calif.). Briefly, reverse-transcribed RNA from test sample and normal liver pool were differentially labelled with fluorescent Cy5-dCTP or Cy3-dCTP. Labelled cDNAs were co-hybridised onto 19K cDNA arrays (Ontario Cancer Institute, Canada). Hybridised signals captured by ScanArray 5000 (Packard BioScience, UK) were analysed by GenePix Pro4.0 (Axon, Calif.). Results from duplicate spots and dye swap experiments were averaged, and the normalized intensity ratio for each transcript was subjected to informatic analysis to determine the influential genes involved in the malignant HCC transformation.

TABLE 1

Demographic Information of 43 HCC Patients Studied by Gene Expression Profiling

|  | HCC Patients (n = 43) |
|---|---|
| Gender | |
| Male | 35 (81.4%) |
| Female | 8 (18.6%) |
| Age | |
| Median (quartiles) | 58 (50-67) |
| HBsAg | |
| Positive | 40 (93.0%) |
| Negative | 3 (7.0%) |
| Underlying Liver Cirrhosis | |
| Present | 37 (86.0%) |
| Absent | 6 (14.0%) |
| AJCC Staging | |
| Stage T1 | 6 (14.0%) |
| Stage T2 | 23 (53.5%) |
| Stage T3 | 10 (23.3%) |
| Stage T4 | 4 (9.3%) |
| No. of Lesions at Presentation | |
| Single | 27 (62.8%) |
| Multiple | 16 (37.2%) |

A combined parametric and non-parametric analysis was performed on the microarray profiles obtained. Statistical significance (P-value) for each gene was calculated based on a pair-wise permutation t-test using Significant Analysis for Microarray (SAM) and paired Wilcoxon signed rank test. Correction for multiple hypotheses testing had also been carried out using Bonferonni or False Discovery Rate analysis.

In order to establish the significance of a gene, the combined P-value from SAM and Wilcoxon tests was averaged, and scored for precedence by ranking. Genes that ranked top 5% percentile (at ≥1.8-fold median up- or down-regulation) were selected and further subjected to functional ontology analysis by Ingenuity Pathway Analysis (IPA; world wide web at ingenuity.com).

Cell Culture and Taxane Drugs

Human liver cancer cell lines Hep3B and SK-HEP1 acquired from ATCC were cultured in Dulbecco's modified Eagle medium with Glutamax-1 (Gibco-BRL, Grand Island, N.Y., USA) supplemented with 10% fetal bovine serum. HKCl-9 (as described in Chan K.Y.Y. et al., *Modern Pathology* 19:1546-54 (2006)) was cultured in AIMV medium (Gibco-BRL) supplemented with 1% L-Glutamine and 10% fetal bovine serum. All cells were cultured under a humidified atmosphere of 5% $CO_2$ at 37° C.

Doxorubicin was obtained from EBEWE Pharma Ges (Unterach, Austria), and stored at a concentration of 2 mg/ml at 4° C. Paclitaxel (Taxol®) was obtained from Bristol-Myers Squibb (Princeton, N.J., USA), and stored at a concentration of 6 mg/ml in 527 mg of purified Cremophor EL and 49.7% dehydrated alcohol at −20° C. Docetaxel (Taxotere®) was obtained from Aventis Pharma SA (Paris, France), and stored at a concentration of 10 mg/ml in 13% w/w ethanol at 4° C. The nanoparticle albumin-bound (nab)-Paclitaxel (Nab-Paclitaxel) was used in this experiment. Each vial of Nab-paclitaxel supplied contains 100 mg of paclitaxel, stabilized in 900 mg of albumin. Upon reconstitution, 20 ml of PBS was added to give a stock concentration of 5 mg/ml Nab-paclitaxel and stored at −20° C. until use.

Cell Viability Assay

Cell viability was measured by MTT Assay. Cells grown in 96-well plates at density of 3000 cells per well were treated with drugs or siRNA transfection as indicated. Paclitaxel, Docetaxel and Nab-Paclitaxel were tested at different concentrations ranging from 0 to 40 μg/ml for 48 h, while Doxorubicin was tested at concentrations ranging from 0 to 150 μg/ml for 48 h. The formazan formed was measured at 570 nm and cell viability is expressed as a percentage of maximum absorbance from 5 replicates in 3 independent experiments. The concentration of drug that inhibited cell survival by 50% (IC50) was determined from cell survival curves.

Immunofluorescence Analysis

Cells plated on sterile 18×18 mm glass cover slip were allowed to adhere for 24 hours prior to treatment with 5 ng/ml Nab-Paclitaxel or medium for another 24 h. Cells fixed in 4% paraformaldehyde were then incubated with anti-β-tubulin (Zymed, Invitrogen) at 1:100 dilution. Secondary antibody Alexa-598-coupled anti-mouse immunoglobulin (Molecular Probes, Eugene, Oreg., USA) was applied at 1:200 dilution. Cell nuclei counterstained in DAPI (Molecular Probes) were examined under a fluorescence microscope (Nikon EFD-3, Japan). Post-capture image analysis and processing of image stacks were performed using the analySIS software.

Flow Cytometry Analysis of Cell Cycle

Cell cycle distribution was measured after exposure to different concentrations of Nab-Paclitaxel. After 12 h, all cells including detached cells were harvested and fixed in 70% ethanol at 4° C. overnight. Fixed cells were incubated with RNase A and propidium iodide prior to flow cytometric analysis (BD FACSCalibur™ Becton Dickinson). The average value of $G_0$-$G_1$, S and $G_2$-M phases were calculated from 2 independent experiments.

TUNEL Assay

TUNEL assay was conducted according to procedures of In-Situ Cell Death Detection Kit (Roche Applied Science, Mannheim, Germany). In brief, cells treated with different concentrations of Nab-Paclitaxel were fixed and incubated with TUNEL reaction mixture for 1 h at 37° C. Cell nuclei counterstained in DAPI were examined by fluorescence microscope (Nikon EFD-3, Japan). Percentage apoptotic cells were calculated based on at least four randomly selected fields, which totaled to about 200 cells.

siRNA Transfection siRNA sequences included STMN1 siGENOME SMARTpool (si-STMN1) and siCONTROL Non-Targeting siRNA (si-mock). All siRNAs were chemically synthesized as double stranded RNA (Dharmacon) and introduced into cell lines by Lipofectamine 2000 (Invitrogen, Carlsbad, Calif., USA) according to manufacturer's instructions. Briefly, cells were incubated with 100 nM siRNA (si-STMN1 or si-mock). Six hours after transfection, medium was replaced by fresh growing medium. The expression of STMN1 was monitored by Western blot, which indicated a repressed expression for at least 3 days. Paclitaxel and Nab-Paclitaxel at concentrations ranging from 0 to 40 μg/ml were applied at $6^{th}$ hour after siRNA transfections. MTT assay for cell viability was carried out at 48 h, and the IC50 values were calculated.

Immunoblotting

Protein lysates from cells treated with Nab-Paclitaxel for 48 h and untreated control cells were quantified using the Bradford Protein Assay (Bio-Rad Laboratories, Hercules, Calif., USA). Equal amounts of protein lysates (30-60 μg) were separated by SDS-PAGE and electrotransferred to nitrocellulose membrane (Bio-Rad Laboratories). Primary antibodies used included anti-STMN1 (1:1000 dilution), anti-PARP (1:1000 dilution) (Santa Cruz Biotechnology, Heidelberg, Germany), anti-GAPDH (1:10,000 dilution) (Millipore Corporation, Bedford, Mass., USA). After incubation with peroxidase conjugated secondary antibody (1:10,000 dilution for anti-GAPDH; 1:2000 for other primary antibodies) (Santa Cruz), protein expression was detected using SuperSignal West Pico Chemiluminescent Substrate (Thermo Scientific, Rockford, Ill., USA).

SK-HEP1/Luc+ Xenograft Model

SK-HEP1 luciferase stable clone was prepared by transfecting SK-HEP1 cells with firefly luciferase expression vector and selected with 500 ug/ml Geneticin (Gibco-BRL) for 4 weeks. Individual colonies were screened for bioluminescence activity using the Xenogen IVIS® imager (Alameda, Calif., USA). Clones with stable luminescence expression were used for in-vivo studies.

Male BALB/c nude mice at 6-8 weeks old with an average body weight of about 20 g were anesthetized by intraperitoneal injection of ketamine hydrochloride (120 mg/kg) (Fort Dodge Animal Health, Fort Dodge, Iowa, USA) plus xylazine (6 mg/kg) (Phoenix Scientific, Inc., St. Joseph, Mo., USA). Anesthetized animals then received $5 \times 10^6$ SK-HEP1/Luc+ cells suspended in 200 μl serum free medium by subcutaneous injection below the dorsal flank. Drug treatments started on day 14 after tumor cells inoculation. Mice were divided into 5 groups: PBS (n=13), Nab-Paclitaxel (n=14), Paclitaxel (n=9), Docetaxel (n=9) and Doxorubicin, (n=10). All drugs were given every two days for five times, at a dose of 35 mmol/kg. See Desai N. et al., *Clinical Cancer Research*, 12:1317-24 (2006). Tumor growth was monitored twice weekly by in-vivo bioluminescent imaging and by external caliper measurements using the formula of [(Length× $Width^2$)/2] for 24 days. For in-vivo bioluminescent imaging, 150 mg/kg D-luciferin were given by intraperitoneal injection and ten minutes after luciferin injection, mice were anesthetized by isoflurane and tumor cell viability was measured by the Xenogen IVIS® imager.

Statistical Analysis

The data was presented as mean±SD. Student's t-test, Kaplan-Meier survival curves and one-way ANOVA analysis were performed using Graphpad Prism 3.0 software. Differences were considered statistically significant at P<0.05.

Results

Functional Ontologies Involved in HCC Development

Genes from the microarray dataset were first ranked and selected by evidence of significant differential expression according to statistical methods. IPA analysis of ~1,000 significant known genes (top 5% percentile changes) suggested a few significant gene ontologies, which included cellular assembly and organization, cellular function and maintenance, cell death, cell cycle, cellular composition, drug and lipid metabolism and small molecules biochemistry (FIG. 1). In particular, the cellular assembly and organization category ranked the most significant event, where over-representations of microtubules associated genes such as STMN1 and TUBB4 were found (FIG. 1).

Cytotoxic Effect of Taxanes on HCC Cells

Figure 2:
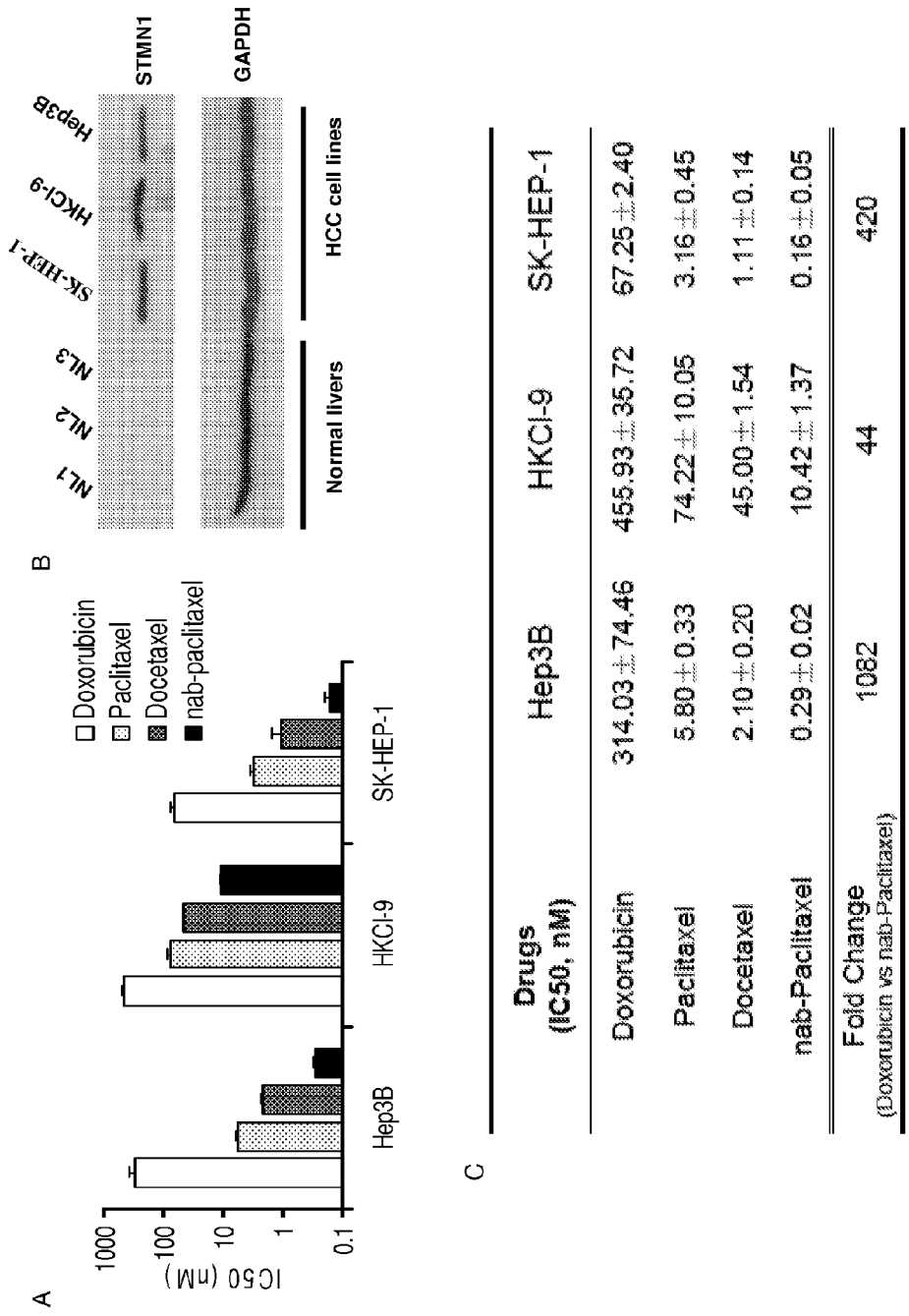
FIG. 2A shows cytotoxic effects of Taxanes and Doxorubicin in HCC. Cell lines Hep3B, HKCl-9 and SK-HEP-1 were treated with increasing concentrations of Doxorubicin, Paclitaxel (Taxol®), Docetaxel (Taxotere®), and Nab-Paclitaxel (Abraxane®) for 48 hours. Effect on cell viability was investigated by MTT, and the IC50 values were determined. Experiments were repeated three times and expressed as the mean±SD.
FIG. 2B shows the expression of STMN1 in normal livers and HCC cell lines as detected by Western blotting.
FIG. 2C shows the IC50 value of drugs tested in different HCC cell lines.

The effects of Paclitaxel, Docetaxel, and Nab-Paclitaxel on HCC cell lines that displayed elevated STMN1 expressions were evaluated (FIG. 2B). A high sensitivity towards the Taxane-based drugs was generally found in Hep3B, SK-HEP1 and HKCl-9 compared to Doxorubicin, a chemotherapeutic agent that is widely used for many cancers, including HCC (FIG. 2A). Remarkably, Nab-Paclitaxel showed the highest potency with a lowest effective dosage found in all 3 cell lines tested. The IC50 obtained on Nab-Paclitaxel ranged from 0.29±0.02 nM to 10.42±1.37 nM, which was about 44-fold to 1082-fold less than Doxorubicin (IC50 value ranged from 105.95±10.58 nM to 455.93±35.72 nM) (FIG. 2C).

Nab-Paclitaxel Treatment Induced Cell Cycle Blockade and Apoptosis

Figure 4:
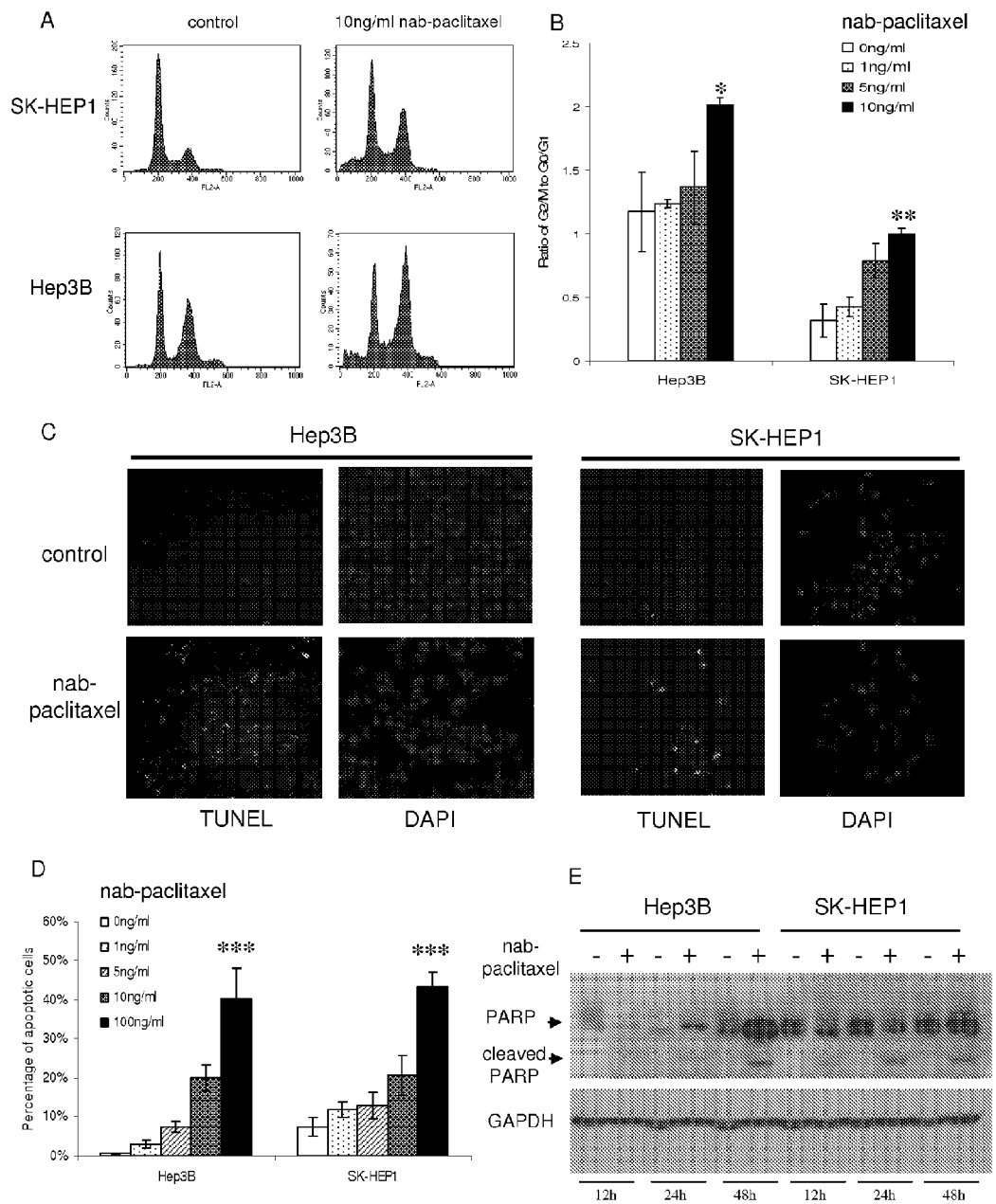
FIG. 4A shows cell cycle profiles of Nab-Paclitaxel treated Hep3B and SK-HEP1. Cells treated with differing concentrations of Nab-Paclitaxel for 12 hour were harvested, stained with PI, and analyzed by flow cytometry.
FIG. 4B shows the ratio of G2M to G0/G1 populations in Hep3B and SK-HEP1 in response to varying concentrations of Nab-Paclitaxel. *$P<0.05$, **$P<0.01$ (One-way ANOVA).
FIG. 4C shows TUNEL analysis in Hep3B and SK-HEP1 cells showed an increase in the number of apoptotic cells after treatment of Nab-Paclitaxel at 100 ng/ml for 48 hours. Nuclei counterstained with DAPI. Images shown are representative of two independent experiments.
FIG. 4D shows the percentage of apoptotic cells increase with increasing concentrations of Nab-Paclitaxel applied. *$P<0.05$, **$P<0.01$ (One-way ANOVA).
FIG. 4E shows Western blot for PARP in Hep3B and SK-HEP1 treated with Nab-Paclitaxel, which demonstrates an increasing amount of cleaved PARP with time.

A higher degree of microtubule polymerization was found in the Nab-paclitaxel treated cells (FIGS. 3A and 3B). Further, in both Hep3B and SK-HEP1, flow cytometric analysis indicated that an increase in the G2/M population was found with increasing concentrations of Nab-Paclitaxel applied, suggesting a dose-dependent cell cycle arrest (P<0.05; FIG. 4B). Flow cytometry profile also showed a sub-G1 fraction appearing after the treatment with Nab-Paclitaxel (FIG. 4A). The presence of apoptotic cells were further confirmed in SK-HEP1 and Hep3B by TUNEL analysis, which indicated the number of TUNEL positive cells corresponded to the amount of Nab-Paclitaxel used (P<0.001; FIG. 4C and FIG. 4D). The cleavage of nuclear protein PARP was determined by monitoring the presence of 89 kDa cleaved product. PARP cleavage became evident at 12 hours after treatment and gradually increased over 48 h (FIG. 4E).

Effect of Nab-Paclitaxel on in-vivo Xenograft Growth

Figure 5:
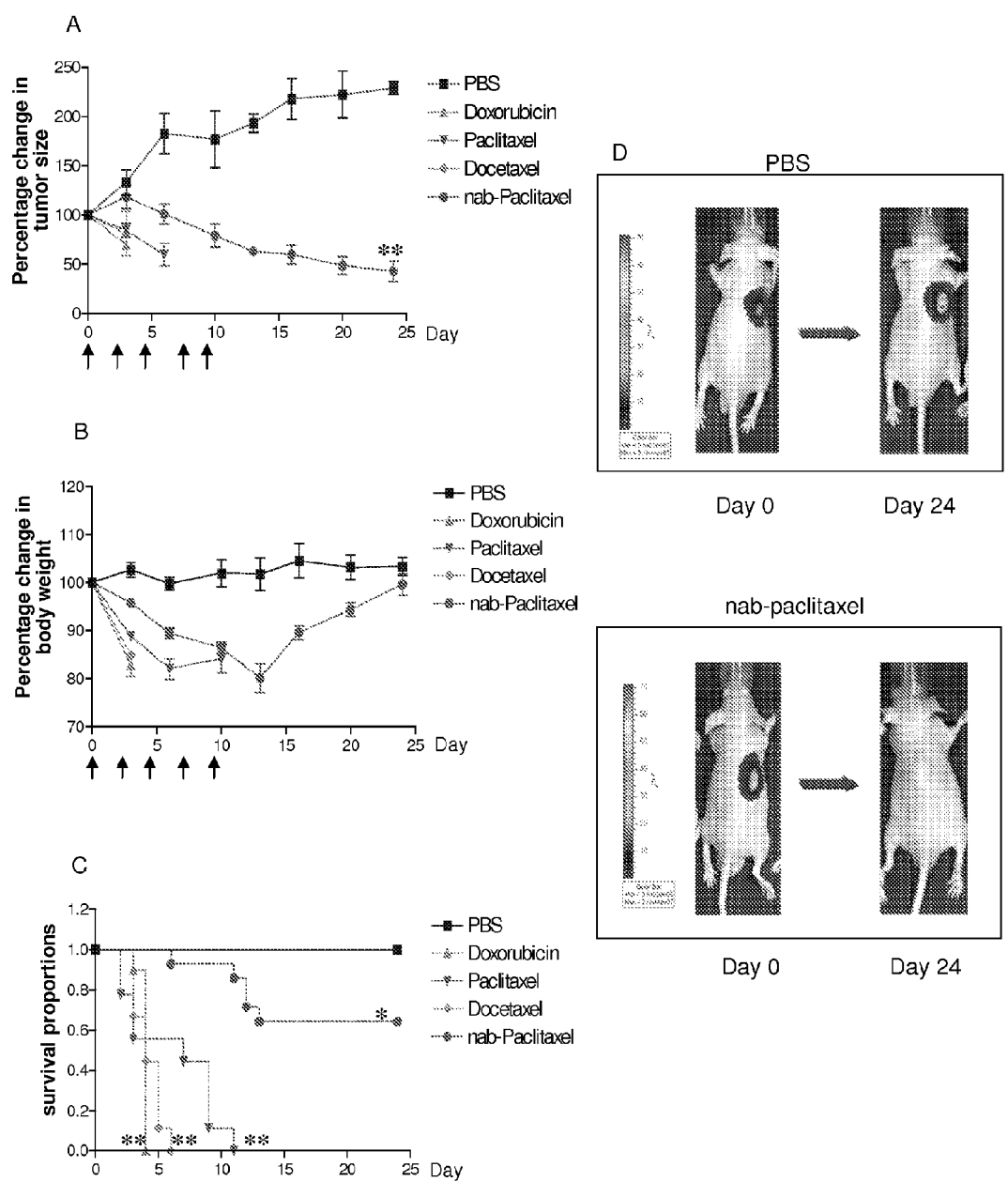
FIG. 5A shows the effect of Nab-Paclitaxel on HCC tumor growth in vivo.
FIG. 5B shows percentage changes in body weight of mice from drug treatments.
FIG. 5C shows survival curves plotted according to the mouse status during experiments. A significant difference between the vehicle group and drug treated groups was observed (*$P<0.05$, **$P<0.01$, compared to PBS group).
FIG. 5D shows the IVIS images of representative control and Nab-Paclitaxel treated mice.

SK-HEP1/Luc+ cells were subcutaneously injected into BALB/c nude mice, and the anti-tumoral effects of various compositions in-vivo were examined. Developed xenograft was measured for tumor size on the first day of treatment and twice weekly thereafter by IVIS imaging and caliper measurements. FIG. 5A shows the percentage change of tumor size in each treatment group with time. The control PBS group showed a gradual increase in tumor size over the period of study. While each treatment group showed a reduction in tumor size, the toxicities from Doxorubicin, Paclitaxel and Docetaxel were particularly severe, which resulted in much weight loss and deaths of many mice within 3 injections (FIG. 5B and FIG. 5C). Although weight loss was also observed with Nab-Paclitaxel injection, it was least severe and the mice were generally able to re-gain body weight after the last injection on Day 9. The anti-tumoral effect of Nab-Paclitaxel was highly significant with considerable inhibition on tumor sizes compared to control group (P=0.0007). Moreover, more than 60% of mice survived to the end of experiments (FIG. 5B).

STMN1 Knockdown Increases Sensitivity to Taxane Drugs

Figure 6:
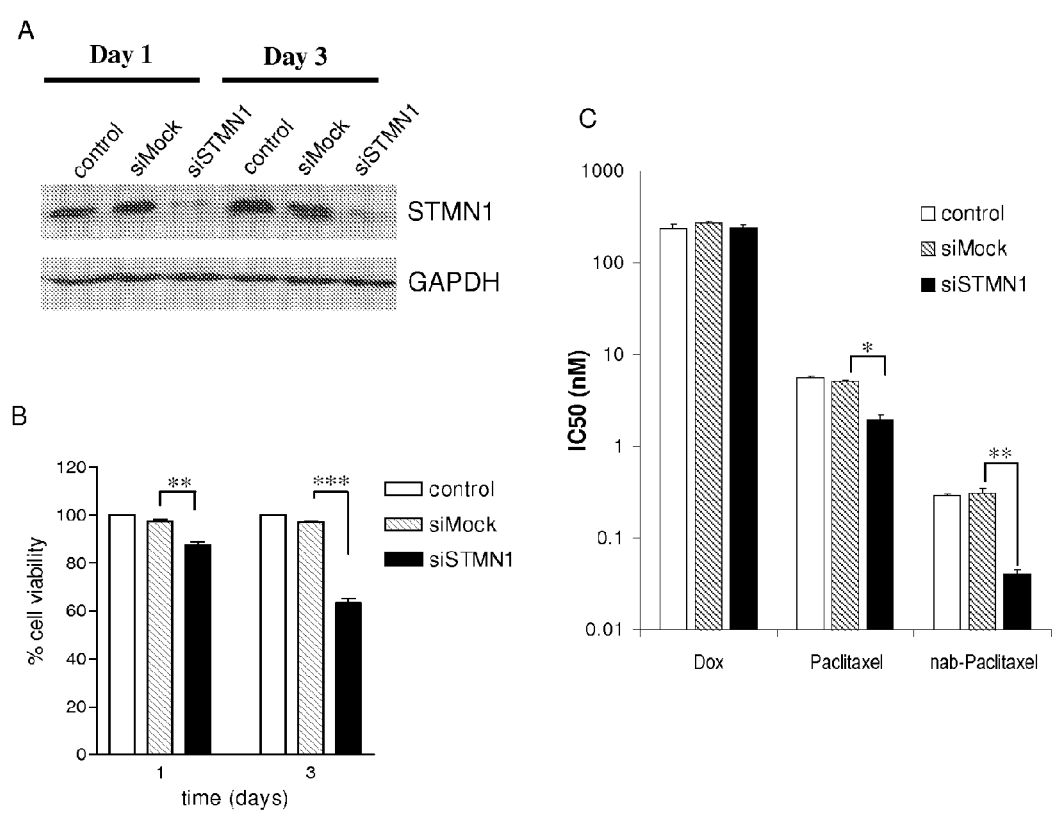
FIG. 6 shows the effect on drug sensitivity following silencing of STMN1 gene expression.

We have observed synergy between STMN know-down and Nab-paclitaxel. FIG. 6A shows the STMN1 protein level in Hep3B after siRNA knockdown on day 1 and day 3. Specific STMN1 knockdown in Hep3B showed ~40% decrease in cell viability compared to mock on Day 3 post-transfection (FIG. 6B). In the combinatory study with the taxanes, Hep3B transfected with si-STMN1 was 7.7-fold more sensitive to Nab-Paclitaxel (IC50, 0.04±0.004 nM vs 0.31±0.04 nM) and 2.7-fold more sensitive to Paclitaxel (IC50, 1.95±0.28 nM vs 5.17±0.06 nM) (FIG. 6C). In contrast, knockdown of STMN1 had no effect on the sensitivity of Doxorubicin, a drug that does not target the microtubules.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating hepatocellular carcinoma (HCC) in an individual in need thereof, comprising administering to the individual: a) an effective amount of a composition comprising nanoparticles comprising a taxane and an albumin, and b) an effective amount of at least one other agent, wherein said other agent is a small interference RNA (siRNA) against STMN1 or an antisense oligonucleotide against STMN1.

2. The method of claim 1, wherein the nanoparticle composition and the other agent are administered simultaneously or sequentially.

3. The method of claim 1, wherein the nanoparticle composition and the other agent are administered concurrently.

4. The method of claim 1, wherein the other agent inhibits a molecule that promotes microtubule disassembly directly or indirectly.

5. The method of claim 1, wherein the other agent is an siRNA against STMN1.

6. The method of claim 1, wherein the HCC is liver cell carcinoma, fibrolamellar variant of HCC, or mixed hepatocellular cholangiocarcinoma.

7. The method of claim 1, wherein the HCC is early stage HCC, non-metastatic HCC, primary HCC, advanced HCC, locally advanced HCC, metastatic HCC, HCC in remission, recurrent HCC, HCC in an adjuvant setting, or HCC in a neoadjuvant setting.

8. The method of claim 1, wherein the composition comprising nanoparticles comprising a taxane and albumin is administered parenterally.

9. The method of claim 8, wherein the composition comprising nanoparticles comprising a taxane and albumin is administered intravenously, intraarterially, intrahepatically, or intraportally.

10. The method of claim 1, wherein the taxane is paclitaxel.

11. The method of claim 1, wherein the nanoparticles in the composition have an average diameter of no greater than about 200 nm.

12. The method of claim 11, wherein the nanoparticles in the composition have an average diameter of less than about 200 nm.

13. The method of claim 1, wherein the taxane in the nanoparticles are coated with albumin.

14. The method of claim 1, wherein the individual is human.

* * * * *